US010533046B2

(12) United States Patent
Albaret et al.

(10) Patent No.: US 10,533,046 B2
(45) Date of Patent: Jan. 14, 2020

(54) ANTI-CK8 ANTIBODIES FOR USE IN THE TREATMENT OF COLORECTAL CANCERS

(71) Applicants: INTERNATIONAL—DRUG—DEVELOPMENT—BIOTECH, Lyons (FR); UNIVERSITE CLAUDE BERNARD LYON 1, Villeurbanne (FR); HOSPICES CIVILS DE LYON, Lyons (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); CENTRE LEON BERARD, Lyons (FR)

(72) Inventors: Marie Alexandra Albaret, Lille d'Abeau (FR); Jean-Jacques Diaz, Venissieux (FR); Hichem Claude Mertani, Lyons (FR); Jean-Christophe Saurin, Lyons (FR); Claudine Vermot-Desroches, Dardilly (FR); Boris Vuillermoz, Les Cheres (FR)

(73) Assignees: INTERNATIONA—DRUG—DEVELOPMENT—BIOTECH, Lyons (FR); UNIVERSITE CLAUDE BERNARD LYON 1, Villeurbanne (FR); HOSPICES CIVILS DE LYON, Lyons (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); CENTRE LEON BERARD, Lyons (FR)

( * ) Notice: Subject to any disclaimer, the term of this patent is extended or adjusted under 35 U.S.C. 154(b) by 57 days.

(21) Appl. No.: 15/502,469

(22) PCT Filed: Aug. 10, 2015

(86) PCT No.: PCT/EP2015/068400
§ 371 (c)(1),
(2) Date: Feb. 7, 2017

(87) PCT Pub. No.: WO2016/020553
PCT Pub. Date: Feb. 11, 2016

(65) Prior Publication Data
US 2018/0237508 A1    Aug. 23, 2018

(30) Foreign Application Priority Data
Aug. 8, 2014    (FR) ..................... 14 57704

(51) Int. Cl.
C07K 16/18    (2006.01)
C07K 16/30    (2006.01)
A61P 35/00    (2006.01)
A61K 39/395    (2006.01)
C07K 7/06    (2006.01)
A61K 39/00    (2006.01)
A61K 45/06    (2006.01)
G01N 33/574    (2006.01)

(52) U.S. Cl.
CPC ........ *C07K 16/18* (2013.01); *A61K 39/39558* (2013.01); *A61K 45/06* (2013.01); *A61P 35/00* (2018.01); *C07K 7/06* (2013.01); *C07K 16/3015* (2013.01); *C07K 16/3046* (2013.01); *C07K 16/3061* (2013.01); *G01N 33/57419* (2013.01); *A61K 39/00* (2013.01); *A61K 2039/505* (2013.01); *A61K 2039/545* (2013.01); *C07K 2317/24* (2013.01); *C07K 2317/34* (2013.01); *C07K 2317/565* (2013.01); *C07K 2317/73* (2013.01); *C07K 2317/76* (2013.01); *G01N 2410/00* (2013.01)

(58) Field of Classification Search
None
See application file for complete search history.

(56) References Cited

U.S. PATENT DOCUMENTS 8,778,341 B2    7/2014    Diaz et al.

FOREIGN PATENT DOCUMENTS

WO    2010/136536 A1    12/2010
WO    WO2016/020553    *    2/2016    ............. C07K 16/18

OTHER PUBLICATIONS

Lloyd et al., Protein Engineering, Design & Selection, 22, 159-168, 2009. (Year: 2009).*
Rudikoff et al., Single amino acid substitution altering antigen-binding specificity. Proc. Natl. Acad. Sci. USA, 79, 1979-1983, 1982. (Year: 1982).*
Lee et al., MCF-7 cells—changing the course of breast cancer research and care for 45 years. J. Natl. Cancer. Inst. 107, 1-4, 2015. (Year: 2015).*
Marie Alexandra Albaret, et al., "Externalized Keratin 8: A Target at the Interface of Microenvironment and Intracellular Signaling in Colorectal Cancer Cells," Cancers 2018, 10, 452; doi:10.3390/cancers10110452.

(Continued)

*Primary Examiner* — Elly-Gerald Stoica
(74) *Attorney, Agent, or Firm* — Arrigo, Lee, Guttman & Mouta-Bellum LLP

(57) ABSTRACT

The present disclosure relates to a human CK8 antigen peptide, an antibody, or antibody fragment thereof, or a humanized antibody, specifically binding the peptide having the amino acid sequence of SEQ ID No. 29, a fragment of CK-8. Said molecules can be used use in the detection and/or treatment of tumors whose cells express CK8 protein, in particular the peptide of sequence according to SEQ ID No.29, on their surface.

18 Claims, 23 Drawing Sheets
Specification includes a Sequence Listing.

(56) References Cited

OTHER PUBLICATIONS

Fortunato Ciardiello, et al., "EGFR Antagonists in Cancer Treatment," N Engl J Med 2008;358:1160-74.

Adrienne D. Cox, et al., "Drugging the undruggable RAS: Mission Possible?," Nature Reviews Drug Discovery, AOP, published online Oct. 17, 2014; doi:10.1038/nrd4389.

David Cunningham, et al., "Cetuximab Monotherapy and Cetuximab plus Irinotecan in Irinotecan-Refractory Metastatic Colorectal Cancer," N Engl J Med 2004;351:337-45.

Elena I. Deryugina and James P. Quigley, "Cell Surface Remodeling by Plasmin: A New Function for an Old Enzyme," Journal of Biomedicine and Biotechnology vol. 2012, Article ID 564259, 21 pages doi:10.1155/2012/564259.

Bojan Doljak, et al., "Monoclonal antibody to cytokeratin VKIALEVEIATY sequence motif reduces plasminogen activation in breast tumour cells," Cancer Letters 267 (2008) 75-84.

Ann Erlandsson, et al., "Studies of the interactions between the anticytokeratin 8 monoclonal antibody TS1, its antigen and its anti-idiotypic antibody TS1," J. Mol. Recognit. 2003; 16: 157-163.

Tarek G. Gharib, et al., "Proteomic Analysis of Cytokeratin Isoforms Uncovers Association with Survival in Lung Adenocarcinoma," Neoplasia.vol. 4, No. 5, 2002,pp. 440-448.

Olivier Gires, et al., "Cytokeratin 8 associates with the external leaflet of plasma membranes in tumour cells," Biochemical and Biophysical Research Communications 328 (2005) 1154-1162.

Olivier Gires, et al., "CK8 correlates with malignancy in leukoplakia and carcinomas of the head and neck," Biochemical and Biophysical Research Communications 343 (2006) 252-259.

Edmond Godfroed, et al., "Cytokeratins are exposed on the outer surface of established human mammary carcinoma cells," Journal of Cell Science 99, 595-607 (1991).

Todd A. Hembrough, et al., "A cytokeratin 8-like protein with plasminogen-binding activity is present on the external surfaces of hepatocytes, HepG2 cells and breast carcinoma cell lines," Journal of Cell Science 108, 1071-1082 (1995).

Amanda Johansson, et al., "Epitope Specificity of the Monoclonal Anticytokeratin Antibody TS1," Cancer Research 59, 48-51, Jan. 1, 1999.

Christos S. Karapetis, et al., "K-ras Mutations and Benefit from Cetuximab in Advanced Colorectal Cancer," n engl j med 359;17, Oct. 23, 2008.

Kristen R. Kralovich, et al., "Characterization of the Binding Sites for Plasminogen and Tissue-Type Plasminogen Activator in Cytokeratin 8 and Cytokeratin 18," Journal of Protein Chemistry, vol. 17, No. 8, 1998.

Shiqing Li, et al., "Structural basis for inhibition of the epidermal growth factor receptor by cetuximab," Cancer Cell : Apr. 2005—vol. 7, pp. 301-311.

Bert Schutte, et al., "DEDD association with cytokeratin filaments correlates with sensitivity to apoptosis," Apoptosis (2006) 11:1561-1572.

Eric Van Cutsem, et al., "Cetuximab and Chemotherapy as Initial Treatment for Metastatic Colorectal Cancer," n engl j med 360;14, Apr. 2, 2009.

Goos N. P. Van Muijen, et al., "Coexpression of Intermediate Filament Polypeptides in Human Fetal and Adult Tissues," Laboratory Investigation, vol. 57, No. 4, p. 359, 1987.

Ahmad Waseem, et al., "Conformational Changes in the Rod Domain of Human Keratin 8 following Heterotypic Association with Keratin 18 and Its Implication for Filament Stability," Biochemistry 2004, 43, 1283-1295.

Jürgen Weitz, et al., "Colorectal cancer," Lancet 2005; 365: 153-65.

\* cited by examiner

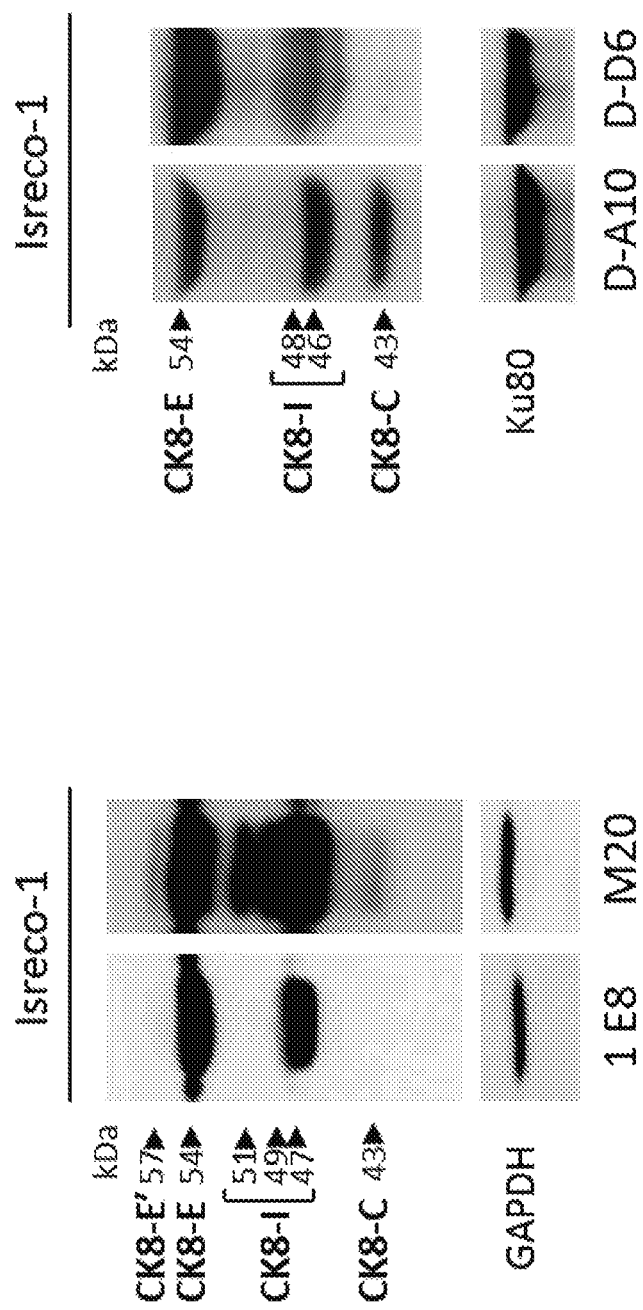

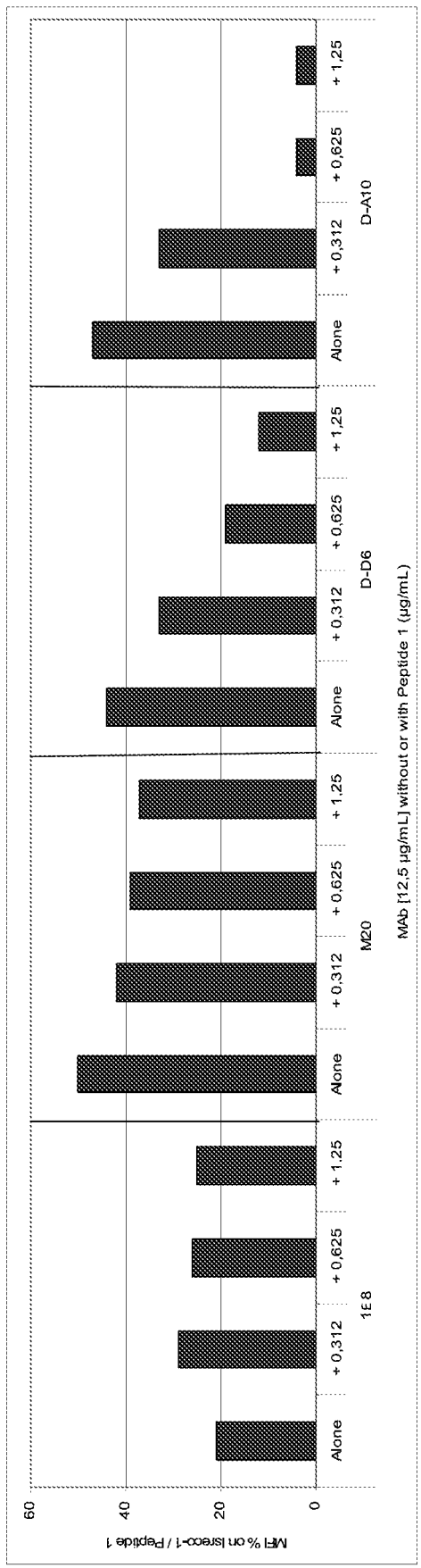
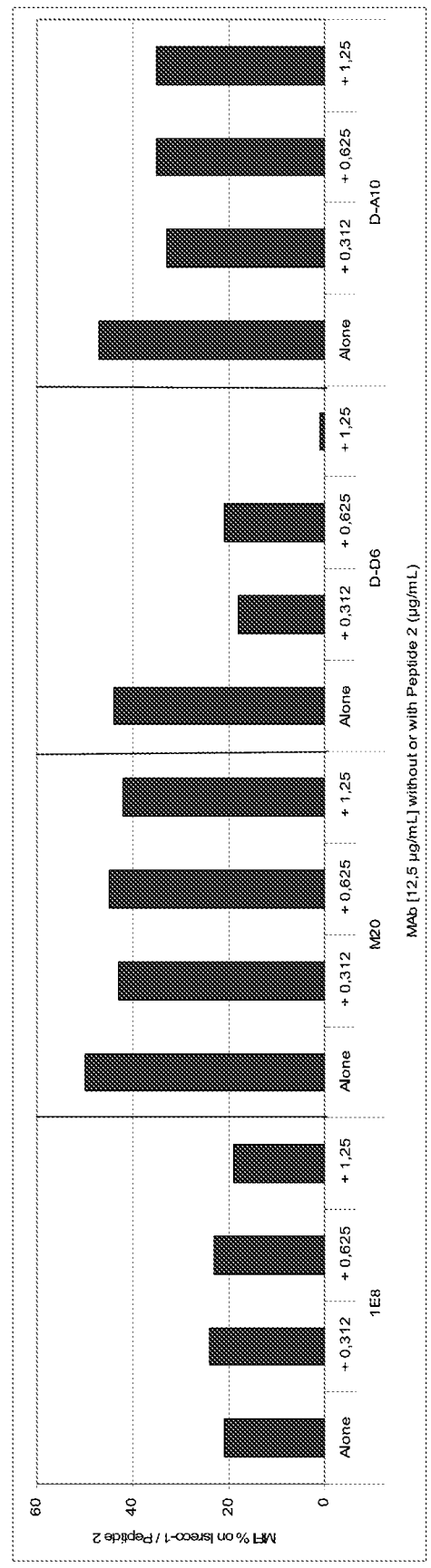

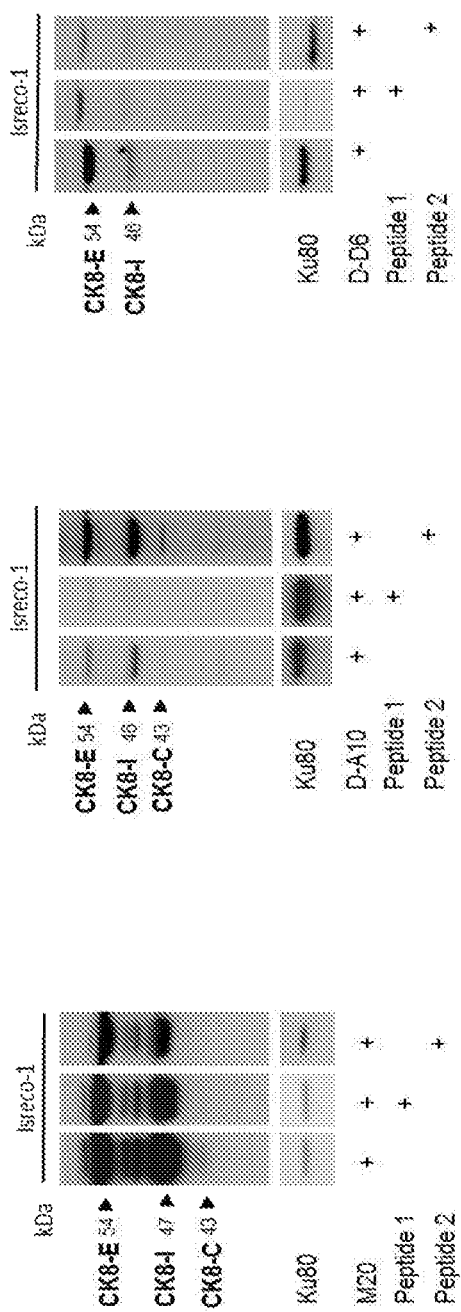

MSIRVTQKSY KVSTSGPRAF SSRSYTSGPG SRISSSSFSR VGSSNFRGGL GGGYGGASGM
GGITAVTVNQ SLLSPLVLEV DPNIQAVRTQ EKEQIKTLNN KFASFIDKVR FLEQQNKMLE
TKWSLLQQQK TARSNMDNMF ESYINNLRRQ LETLGQEKLK LEAELGNMQG LVEDFKNKYE
DEINKRTEME NEFVLIKKDV DEAYMNKVEL ESRLEGLTDE INFLRQLYEE EIRELQSQIS
DTSVVLSMDN SRSLDMDSII AEVKAQYEDI ANRSRAEAES MYQIKYEELQ SLAGKHGDDL
RRTKTEISEM NRNISRLQAE IEGLKGQRAS LEAAIADAEQ RGELAIKDAN AKLSELEAAL
QRAKQDMARQ LREYQELMNV KLALDIEIAT YRKLLEGEES RLESGMQNMS IHTKTTSGYA
GGLSSAYGGL TSPGLSYSLG SSFGSGAGSS SFSRTSSSRA VVVKKIETRD GKLVSESSDV
LPK

FIG. 11

```
<----------------------- H-FR1-IMGT ------------------------
GAA GTG CAG CTG TTG GAG ACT GGA GGC TTG GTG CAA CCG GGG GGG TCA CGG GGA
 E   V   Q   L   L   E   T   G   G   L   V   Q   P   G   G   S   R   G
-------->  <------------ H-CDR1-IMGT -------->
CTC TCT TGT GAA GGC TCA GGG TTT ACT TTT AGT GGC TTC TGG ATG AGC TGG GTT CGA
 L   S   C   E   G   S   G   F   T   F   S   G   F   W   M   S   W   V   R
<------------ H-FR2-IMGT ------------>   <---- H-CDR2-IMGT
CAG ACA CCT GGG AAG GGC CTG GAG TGG ATT GGA GAC ATT AAT TCT GAT GGC AGT GCA
 Q   T   P   G   K   G   L   E   W   I   G   D   I   N   S   D   G   S   A
---->  <------------------ H-FR3-IMGT --------------------
ATA AAA TAC GCA CCA TCC ATA AAG GAT CGA TTC ACT ATC TCC AGA GAC AAT GCC AAG
 I   K   Y   A   P   S   I   K   D   R   F   T   I   S   R   D   N   A   K
-------------------->  <----------- H-CDR3-IMGT
AGC ACC CTG TAC CTG CAA ATG AGC AAT GTG CGA TCT GAG GAC ACA GCC ACG TAT TTC
 S   T   L   Y   L   Q   M   S   N   V   R   S   E   D   T   A   T   Y   F
----------->
TGT ATC GCC CAT TAC TCC GGT GGG GGG TTT GCT TAC TGG GGT CAA GGA ACC TCG GTC
 C   I   A   H   Y   S   G   G   G   F   A   Y   W   G   Q   G   T   S   V

ACC GTC TCC TCA
 T   V   S   S
```

FIG. 17

```
<---------------------- H-FR1-IMGT ----------------------|
GAA GTA CAA TTG GTA GAA TCA GGT GGT TTG GTT CAG CCA GGA GGA TCA CTG AGA
 E   V   Q   L   V   E   S   G   G   L   V   Q   P   G   G   S   L   R

|---------- H-CDR1-IMGT ----------|
CTG TCC TGC GCT GCA AGC GGC TTT ACC TTC TCT AGC TAC TGG ATG TCT TGG GTC CGG
 L   S   C   A   A   S   G   F   T   F   S   S   Y   W   M   S   W   V   R

|------------ H-FR2-IMGT ------------|                |---------- H-CDR2-IMGT
CAA GCC CCA GGG AAG GGA CTG GTG TGG GTG AGC GAT ATT AAT AGT GAC GGC TCT TCT
 Q   A   P   G   K   G   L   V   W   V   S   D   I   N   S   D   G   S   S

----------|         |------------------- H-FR3-IMGT -------------------
ACT AAG TAT GCT GAT AGT GTC AAG GGC CGA TTC ACC ATC TCA CGA GAC AAC GCC AAG
 T   K   Y   A   D   S   V   K   G   R   F   T   I   S   R   D   N   A   K

-------------------|                              |----- H-CDR3-IMGT
AAC ACC TTG TAC CTC CAG ATG AAC TCT TTG AGA GCT GAG GAT ACA GCA GTG TAT TAC
 N   T   L   Y   L   Q   M   N   S   L   R   A   E   D   T   A   V   Y   Y

----------------|
TGT ATC GCC CAC TAC TCA GGG GGA GGC TTT GCT TAC TGG GGT CAA GGC ACA CTC GTG
 C   I   A   H   Y   S   G   G   G   F   A   Y   W   G   Q   G   T   L   V

ACA GTC TCC TCT
 T   V   S   S
```

| GCC | TCC | ACC | AAG | GGC | CCA | TCG | GTC | TTC | CCC | CTG | GCA | CCC | TCC | AAG | AGC | ACC | TCT |
| A | S | T | K | G | P | S | V | F | P | L | A | P | S | K | S | T | S |

CH1

| GGG | GGC | ACA | GCG | GCC | CTG | GGC | TGC | CTG | GTC | AAG | GAC | TAC | TTC | CCC | GAA | CCG | GTG | ACG |
| G | G | T | A | A | L | G | C | L | V | K | D | Y | F | P | E | P | V | T |

| GTG | TCG | TGG | AAC | TCA | GGC | GCC | CTG | ACC | AGC | GGC | GTG | CAC | ACC | TTC | CCG | GCT | GTC | CTA |
| V | S | W | N | S | G | A | L | T | S | G | V | H | T | F | P | A | V | L |

| CAG | TCC | TCA | GGA | CTC | TAC | TCC | CTC | AGC | AGC | GTG | GTG | ACC | GTG | CCC | TCC | AGC | AGC | TTG |
| Q | S | S | G | L | Y | S | L | S | S | V | V | T | V | P | S | S | S | L |

| GGC | ACC | CAG | ACC | TAC | ATC | TGC | AAC | GTG | AAT | CAC | AAG | CCC | AGC | AAC | ACC | AAG | GTG | GAC |
| G | T | Q | T | Y | I | C | N | V | N | H | K | P | S | N | T | K | V | D |

HINGE

| AAG | AAA | GTT | GAG | CCC | AAA | TCT | TGT | GAC | AAA | ACT | CAC | ACA | TGC | CCA | CCG | TGC | CCA | GCA |
| K | K | V | E | P | K | S | C | D | K | T | H | T | C | P | P | C | P | A |

| CCT | GAA | CTC | CTG | GGG | GGA | CCG | TCA | GTC | TTC | CTC | TTC | CCC | CCA | AAA | CCC | AAG | GAC | ACC |
| P | E | L | L | G | G | P | S | V | F | L | F | P | P | K | P | K | D | T |

CH2

| CTC | ATG | ATC | TCC | CGG | ACC | CCT | GAG | GTC | ACA | TGC | GTG | GTG | GTG | GAC | GTG | AGC | CAC | GAA |
| L | M | I | S | R | T | P | E | V | T | C | V | V | V | D | V | S | H | E |

| GAC | CCT | GAG | GTC | AAG | TTC | AAC | TGG | TAC | GTG | GAC | GGC | GTG | GAG | GTG | CAT | AAT | GCC | AAG |
| D | P | E | V | K | F | N | W | Y | V | D | G | V | E | V | H | N | A | K |

| ACA | AAG | CCG | CGG | GAG | GAG | CAG | TAC | AAC | AGC | ACG | TAC | CGT | GTG | GTC | AGC | GTC | CTC | ACC |
| T | K | P | R | E | E | Q | Y | N | S | T | Y | R | V | V | S | V | L | T |

| GTC | CTG | CAC | CAG | GAC | TGG | CTG | AAT | GGC | AAG | GAG | TAC | AAG | TGC | AAG | GTC | TCC | AAC | AAA |
| V | L | H | Q | D | W | L | N | G | K | E | Y | K | C | K | V | S | N | K |

| GCC | CTC | CCA | GCC | CCC | ATC | GAG | AAA | ACC | ATC | TCC | AAA | GCC | AAA | GGG | CAG | CCC | CGA | GAA |
| A | L | P | A | P | I | E | K | T | I | S | K | A | K | G | Q | P | R | E |

TO FIG. 20 (CONT.)

FROM FIG. 20 (CONT.)

```
CCA CAG GTG TAC ACC CTG CCC CCA TCC CGG GAT GAG CTG ACC AAG AAC CAG GTC AGC
 P   Q   V   Y   T   L   P   P   S   R   D   E   L   T   K   N   Q   V   S
                                    CH3
CTG ACC TGC CTG GTC AAA GGC TTC TAT CCC AGC GAC ATC GCC GTG GAG TGG GAG AGC
 L   T   C   L   V   K   G   F   Y   P   S   D   I   A   V   E   W   E   S
AAT GGG CAG CCG GAG AAC AAC TAC AAG ACC ACG CCT CCC GTG CTG GAC TCC GAC GGC
 N   G   Q   P   E   N   N   Y   K   T   T   P   P   V   L   D   S   D   G
TCC TTC TTC CTC TAC AGC AAG CTC ACC GTG GAC AAG AGC AGG TGG CAG CAG GGG AAC
 S   F   F   L   Y   S   K   L   T   V   D   K   S   R   W   Q   Q   G   N
GTC TTC TCA TGC TCC GTG ATG CAT GAG GCT CTG CAC AAC CAC TAC ACG CAG AAG AGC
 V   F   S   C   S   V   M   H   E   A   L   H   N   H   Y   T   Q   K   S
CTC TCC CTG TCT CCG GGT AAA TGA
 L   S   L   S   P   G   K   *
```

FIG. 20 (CONT.)

```
CGA ACT GTG GCT GCA CCA TCT GTC TTC ATC TTC CCG CCA TCT GAT GAG CAG TTG AAA
 R   T   V   A   A   P   S   V   F   I   F   P   P   S   D   E   Q   L   K
TCT GGA ACT GCC TCT GTT GTG TGC CTG CTG AAT AAC TTC TAT CCC AGA GAG GCC AAA
 S   G   T   A   S   V   V   C   L   L   N   N   F   Y   P   R   E   A   K
GTA CAG TGG AAG GTG GAT AAC GCC CTC CAA TCG GGT AAC TCC CAG GAG AGT GTC ACA
 V   Q   W   K   V   D   N   A   L   Q   S   G   N   S   Q   E   S   V   T
GAG CAG GAC AGC AAG GAC AGC ACC TAC AGC CTC AGC AGC ACC CTG ACG CTG AGC AAA
 E   Q   D   S   K   D   S   T   Y   S   L   S   S   T   L   T   L   S   K
GCA GAC TAC GAG AAA CAC AAA GTC TAC GCC TGC GAA GTC ACC CAT CAG GGC CTG AGC
 A   D   Y   E   K   H   K   V   Y   A   C   E   V   T   H   Q   G   L   S
TCG CCC GTC ACA AAG AGC TTC AAC AGG GGA GAG TGT TAG
 S   P   V   T   K   S   F   N   R   G   E   C   *
```

*FIG. 21*

SEQUENCE LISTING

<160> NUMBER OF SEQ ID NOS: 50

<210> SEQ ID NO 1
<211> LENGTH: 30
<212> TYPE: PRT
<213> ORGANISM: Artificial Sequence
<220> FEATURE:
<223> OTHER INFORMATION: Amino acids from position 338 to 366 of human
      CK8, with cystein in C-terminal position

<400> SEQUENCE: 1

Ala Glu Gln Arg Gly Glu Leu Ala Ile Lys Asp Ala Asn Ala Lys Leu
1               5                   10                  15

Ser Glu Leu Glu Ala Ala Leu Gln Arg Ala Lys Gln Asp Cys
            20                  25                  30

<210> SEQ ID NO 2
<211> LENGTH: 21
<212> TYPE: PRT
<213> ORGANISM: Artificial Sequence
<220> FEATURE:
<223> OTHER INFORMATION: Amino acids from position 338 to 357 of human
      CK8, with cystein in C-terminal position

<400> SEQUENCE: 2

Ala Glu Gln Arg Gly Glu Leu Ala Ile Lys Asp Ala Asn Ala Lys Leu
1               5                   10                  15

Ser Glu Leu Glu Cys
            20

<210> SEQ ID NO 3
<211> LENGTH: 10
<212> TYPE: PRT
<213> ORGANISM: Artificial Sequence
<220> FEATURE:
<223> OTHER INFORMATION: Amino acids from position 358 to 366 of human
      CK8, with cystein in C-terminal position

<400> SEQUENCE: 3

Ala Ala Leu Gln Arg Ala Lys Gln Asp Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Amino acids from position 354 to 366 of human
      CK8, with cystein in C-terminal position

<400> SEQUENCE: 4

Ser Glu Leu Glu Ala Ala Leu Gln Arg Ala Lys Gln Asp Cys
1               5                   10

<210> SEQ ID NO 5
<211> LENGTH: 29
<212> TYPE: PRT
<213> ORGANISM: Artificial Sequence
<220> FEATURE:
<223> OTHER INFORMATION: Peptide 5

<400> SEQUENCE: 5

Ala Glu Gln Arg Gly Glu Leu Ala Ile Lys Asp Ala Asn Ala Lys Leu
1               5                   10                  15

Ser Glu Leu Glu Ala Ala Leu Gln Arg Ala Lys Gln Asp
            20                  25

```
<210> SEQ ID NO 6
<211> LENGTH: 9
<212> TYPE: PRT
<213> ORGANISM: Artificial Sequence
<220> FEATURE:
<223> OTHER INFORMATION: Peptide 6

<400> SEQUENCE: 6

Ala Ala Leu Gln Arg Ala Lys Gln Asp
1               5

<210> SEQ ID NO 7
<211> LENGTH: 10
<212> TYPE: PRT
<213> ORGANISM: Artificial Sequence
<220> FEATURE:
<223> OTHER INFORMATION: Peptide 7

<400> SEQUENCE: 7

Glu Ala Ala Leu Gln Arg Ala Lys Gln Asp
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Peptide 8

<400> SEQUENCE: 8

Leu Glu Ala Ala Leu Gln Arg Ala Lys Gln Asp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Peptide 9

<400> SEQUENCE: 9

Glu Leu Glu Ala Ala Leu Gln Arg Ala Lys Gln Asp
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Peptide 10

<400> SEQUENCE: 10

Ser Glu Leu Glu Ala Ala Leu Gln Arg Ala Lys Gln Asp
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Peptide 11

<400> SEQUENCE: 11

Leu Ser Glu Leu Glu Ala Ala Leu Gln Arg Ala Lys Gln Asp
1               5                   10
```

```
<210> SEQ ID NO 12
<211> LENGTH: 15
<212> TYPE: PRT
<213> ORGANISM: Artificial Sequence
<220> FEATURE:
<223> OTHER INFORMATION: Peptide 12

<400> SEQUENCE: 12

Lys Leu Ser Glu Leu Glu Ala Ala Leu Gln Arg Ala Lys Gln Asp
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Peptide 13

<400> SEQUENCE: 13

Ala Lys Leu Ser Glu Leu Glu Ala Ala Leu Gln Arg Ala Lys Gln Asp
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: Peptide 14

<400> SEQUENCE: 14

Asn Ala Lys Leu Ser Glu Leu Glu Ala Ala Leu Gln Arg Ala Lys Gln
1               5                   10                  15

Asp

<210> SEQ ID NO 15
<211> LENGTH: 18
<212> TYPE: PRT
<213> ORGANISM: Artificial Sequence
<220> FEATURE:
<223> OTHER INFORMATION: Peptide 15

<400> SEQUENCE: 15

Ala Asn Ala Lys Leu Ser Glu Leu Glu Ala Ala Leu Gln Arg Ala Lys
1               5                   10                  15

Gln Asp

<210> SEQ ID NO 16
<211> LENGTH: 19
<212> TYPE: PRT
<213> ORGANISM: Artificial Sequence
<220> FEATURE:
<223> OTHER INFORMATION: Peptide 16

<400> SEQUENCE: 16

Asp Ala Asn Ala Lys Leu Ser Glu Leu Glu Ala Ala Leu Gln Arg Ala
1               5                   10                  15

Lys Gln Asp

<210> SEQ ID NO 17
<211> LENGTH: 23
<212> TYPE: PRT
<213> ORGANISM: Artificial Sequence
<220> FEATURE:
<223> OTHER INFORMATION: Peptide 17
```

```
<400> SEQUENCE: 17

Cys Ala Ile Lys Asp Ala Asn Ala Lys Leu Ser Glu Leu Glu Ala Ala
1               5                   10                  15

Leu Gln Arg Ala Lys Gln Asp
            20

<210> SEQ ID NO 18
<211> LENGTH: 21
<212> TYPE: PRT
<213> ORGANISM: Artificial Sequence
<220> FEATURE:
<223> OTHER INFORMATION: Peptide 18

<400> SEQUENCE: 18

Ala Ile Lys Asp Ala Asn Ala Lys Leu Ser Glu Leu Glu Ala Ala Leu
1               5                   10                  15

Gln Arg Ala Lys Gln
            20

<210> SEQ ID NO 19
<211> LENGTH: 20
<212> TYPE: PRT
<213> ORGANISM: Artificial Sequence
<220> FEATURE:
<223> OTHER INFORMATION: Peptide 19

<400> SEQUENCE: 19

Ala Ile Lys Asp Ala Asn Ala Lys Leu Ser Glu Leu Glu Ala Ala Leu
1               5                   10                  15

Gln Arg Ala Lys
            20

<210> SEQ ID NO 20
<211> LENGTH: 19
<212> TYPE: PRT
<213> ORGANISM: Artificial Sequence
<220> FEATURE:
<223> OTHER INFORMATION: Peptide 20

<400> SEQUENCE: 20

Ala Ile Lys Asp Ala Asn Ala Lys Leu Ser Glu Leu Glu Ala Ala Leu
1               5                   10                  15

Gln Arg Ala

<210> SEQ ID NO 21
<211> LENGTH: 18
<212> TYPE: PRT
<213> ORGANISM: Artificial Sequence
<220> FEATURE:
<223> OTHER INFORMATION: Peptide 21

<400> SEQUENCE: 21

Ala Ile Lys Asp Ala Asn Ala Lys Leu Ser Glu Leu Glu Ala Ala Leu
1               5                   10                  15

Gln Arg

<210> SEQ ID NO 22
<211> LENGTH: 17
<212> TYPE: PRT
<213> ORGANISM: Artificial Sequence
<220> FEATURE:
<223> OTHER INFORMATION: Peptide 22
```

<400> SEQUENCE: 22

Ala Ile Lys Asp Ala Asn Ala Lys Leu Ser Glu Leu Glu Ala Ala Leu
1               5                   10                  15

Gln

<210> SEQ ID NO 23
<211> LENGTH: 16
<212> TYPE: PRT
<213> ORGANISM: Artificial Sequence
<220> FEATURE:
<223> OTHER INFORMATION: Peptide 23

<400> SEQUENCE: 23

Ala Ile Lys Asp Ala Asn Ala Lys Leu Ser Glu Leu Glu Ala Ala Leu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Peptide 24

<400> SEQUENCE: 24

Ala Ile Lys Asp Ala Asn Ala Lys Leu Ser Glu Leu Glu Ala Ala
1               5                   10                  15

<210> SEQ ID NO 25
<211> LENGTH: 14
<212> TYPE: PRT
<213> ORGANISM: Artificial sequence
<220> FEATURE:
<223> OTHER INFORMATION: Peptide 25

<400> SEQUENCE: 25

Ala Ile Lys Asp Ala Asn Ala Lys Leu Ser Glu Leu Glu Ala
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Peptide 26

<400> SEQUENCE: 26

Ala Ile Lys Asp Ala Asn Ala Lys Leu Ser Glu Leu Glu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Peptide 27

<400> SEQUENCE: 27

Ala Ile Lys Asp Ala Asn Ala Lys Leu Ser Glu Leu
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Peptide 28

<400> SEQUENCE: 28

Ala Ile Lys Asp Ala Asn Ala Lys Leu Ser Glu
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Amino acids from position 353 to 360 of human
      CK8

<400> SEQUENCE: 29

Leu Ser Glu Leu Glu Ala Ala Leu
1               5

<210> SEQ ID NO 30
<211> LENGTH: 306
<212> TYPE: DNA
<213> ORGANISM: Artificial Sequence
<220> FEATURE:
<223> OTHER INFORMATION: VL mD-A10

<400> SEQUENCE: 30

```
aacattgtta tgacccaggc cgcaccctct gtacctgtca ctcctggaga gtcagtatcc      60
atctcctgca ggtctagtaa gagtcttctg tatagtaatg caacactta tttgtattgg     120 ttcctgcaga ggccaggcca gtctcctcag cgcctgatat attatatgtc caaccttgcc    180
tcaggagtcc cagacaggtt cagtggcaga gggtcaggaa ctgatttcac actgagaatc    240
agtagagtgg aggctgagga tgtgggtgtt tattactgta tgcaaagtct agaatatcct    300
ttcacg                                                                306
```

<210> SEQ ID NO 31
<211> LENGTH: 112
<212> TYPE: PRT
<213> ORGANISM: Artificial Sequence
<220> FEATURE:
<223> OTHER INFORMATION: VL  mD-A10

<400> SEQUENCE: 31

Asn Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu Tyr Ser
                20                  25                  30

Asn Gly Asn Thr Tyr Leu Tyr Trp Phe Leu Gln Arg Pro Gly Gln Ser
            35                  40                  45

Pro Gln Arg Leu Ile Tyr Tyr Met Ser Asn Leu Ala Ser Gly Val Pro
    50                  55                  60

Asp Arg Phe Ser Gly Arg Gly Ser Gly Thr Asp Phe Thr Leu Arg Ile
65                  70                  75                  80

Ser Arg Val Glu Ala Glu Asp Val Gly Val Tyr Tyr Cys Met Gln Ser
                85                  90                  95

Leu Glu Tyr Pro Phe Thr Phe Gly Gly Gly Thr Lys Leu Glu Ile Lys
            100                 105                 110

<210> SEQ ID NO 32
<211> LENGTH: 354
<212> TYPE: DNA
<213> ORGANISM: Artificial Sequence
<220> FEATURE:
<223> OTHER INFORMATION: VH mD-A10

-continued

<400> SEQUENCE: 32

```
gaagtgcagc tgttggagac tggaggaggc ttggtgcaac cggggggtc acggggactc      60
tcttgtgaag gctcagggtt tactttagt ggcttctgga tgagctgggt tcgacagaca     120
cctgggaaga ccctggagtg gattggagac attaattctg atggcagtgc aataaaatac    180
gcaccatcca taaaggatcg attcactatc ttcagagaca atgacaagag caccctgtac    240
ctgcagatga gcaatgtgcg atctgaggac acagccacgt atttctgtat cgcccattac    300
tccggtgggg ggtttgctta ctggggtcaa ggaacctcgg tcaccgtctc ctca           354
```

<210> SEQ ID NO 33
<211> LENGTH: 118
<212> TYPE: PRT
<213> ORGANISM: Artificial Sequence
<220> FEATURE:
<223> OTHER INFORMATION: VH mD-A10

<400> SEQUENCE: 33

Glu Val Gln Leu Leu Glu Thr Gly Gly Gly Leu Val Gln Pro Gly Gly
1               5                   10                  15

Ser Arg Gly Leu Ser Cys Glu Gly Ser Gly Phe Thr Phe Ser Gly Phe
            20                  25                  30

Trp Met Ser Trp Val Arg Gln Thr Pro Gly Lys Thr Leu Glu Trp Ile
        35                  40                  45

Gly Asp Ile Asn Ser Asp Gly Ser Ala Ile Lys Tyr Ala Pro Ser Ile
    50                  55                  60

Lys Asp Arg Phe Thr Ile Phe Arg Asp Asn Asp Lys Ser Thr Leu Tyr
65                  70                  75                  80

Leu Gln Met Ser Asn Val Arg Ser Glu Asp Thr Ala Thr Tyr Phe Cys
                85                  90                  95

Ile Ala His Tyr Ser Gly Gly Gly Phe Ala Tyr Trp Gly Gln Gly Thr
            100                 105                 110

Ser Val Thr Val Ser Ser
        115

<210> SEQ ID NO 34
<211> LENGTH: 11
<212> TYPE: PRT
<213> ORGANISM: Artificial Sequence
<220> FEATURE:
<223> OTHER INFORMATION: CDR1 VL mD-A10

<400> SEQUENCE: 34

Lys Ser Leu Leu Tyr Ser Asn Gly Asn Thr Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: CDR2 VL mD-A10

<400> SEQUENCE: 35

Tyr Met Ser
1

<210> SEQ ID NO 36
<211> LENGTH: 9
<212> TYPE: PRT
<213> ORGANISM: Artificial Sequence

```
<220> FEATURE:
<223> OTHER INFORMATION: CDR3 VL mD-A10

<400> SEQUENCE: 36

Met Gln Ser Leu Glu Tyr Pro Phe Thr
1               5

<210> SEQ ID NO 37
<211> LENGTH: 8
<212> TYPE: PRT
<213> ORGANISM: Artificial Sequence
<220> FEATURE:
<223> OTHER INFORMATION: CDR1 VH mD-A10

<400> SEQUENCE: 37

Gly Phe Thr Phe Ser Gly Phe Trp
1               5

<210> SEQ ID NO 38
<211> LENGTH: 8
<212> TYPE: PRT
<213> ORGANISM: Artificial Sequence
<220> FEATURE:
<223> OTHER INFORMATION: CDR2 VH mD-A10

<400> SEQUENCE: 38

Ile Asn Ser Asp Gly Ser Ala Ile
1               5

<210> SEQ ID NO 39
<211> LENGTH: 11
<212> TYPE: PRT
<213> ORGANISM: Artificial Sequence
<220> FEATURE:
<223> OTHER INFORMATION: CDR3 VH mD-A10

<400> SEQUENCE: 39

Ile Ala His Tyr Ser Gly Gly Gly Phe Ala Tyr
1               5                   10

<210> SEQ ID NO 40
<211> LENGTH: 8
<212> TYPE: PRT
<213> ORGANISM: Artificial Sequence
<220> FEATURE:
<223> OTHER INFORMATION: CDR1 VH HzD-A10

<400> SEQUENCE: 40

Gly Phe Thr Phe Ser Ser Tyr Trp
1               5

<210> SEQ ID NO 41
<211> LENGTH: 8
<212> TYPE: PRT
<213> ORGANISM: Artificial Sequence
<220> FEATURE:
<223> OTHER INFORMATION: CDR2 VH HzD-A10

<400> SEQUENCE: 41

Ile Asn Ser Asp Gly Ser Ser Thr
1               5

<210> SEQ ID NO 42
<211> LENGTH: 11
<212> TYPE: PRT
<213> ORGANISM: Artificial Sequence
```

```
<220> FEATURE:
<223> OTHER INFORMATION: CDR1 VL HzD-A10

<400> SEQUENCE: 42

Lys Ser Leu Leu Tyr Ser Asn Gly Tyr Asn Tyr
1               5                   10

<210> SEQ ID NO 43
<211> LENGTH: 112
<212> TYPE: PRT
<213> ORGANISM: Artificial Sequence
<220> FEATURE:
<223> OTHER INFORMATION: VL  HzD-A10

<400> SEQUENCE: 43

Asp Ile Val Met Thr Gln Ala Pro Leu Ser Leu Pro Val Thr Pro Gly
1               5                   10                  15

Glu Pro Ala Ser Ile Ser Cys Arg Ser Ser Lys Ser Leu Leu Tyr Ser
                20                  25                  30

Asn Gly Tyr Asn Tyr Leu Tyr Trp Phe Leu Gln Lys Pro Gly Gln Ser
            35                  40                  45

Pro Gln Leu Leu Ile Tyr Tyr Met Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Tyr Pro Phe Thr Phe Gly Gln Gly Thr Lys Leu Glu Ile Lys
            100                 105                 110

<210> SEQ ID NO 44
<211> LENGTH: 118
<212> TYPE: PRT
<213> ORGANISM: Artificial Sequence
<220> FEATURE:
<223> OTHER INFORMATION: VH  HzD-A10

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Val Trp Val
            35                  40                  45

Ser Asp Ile Asn Ser Asp Gly Ser Ser Thr Lys Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ala His Tyr Ser Gly Gly Gly Phe Ala Tyr Trp Gly Gln Gly Thr
            100                 105                 110

Leu Val Thr Val Ser Ser
        115

<210> SEQ ID NO 45
<211> LENGTH: 354
<212> TYPE: DNA
<213> ORGANISM: Artificial Sequence
```

```
<220> FEATURE:
<223> OTHER INFORMATION: VH  HzD-A10

<400> SEQUENCE: 45
gaagtacaat tggtagaatc aggtggtggt ttggttcagc caggaggatc actgagactg      60
tcctgcgctg caagcggctt taccttctct agctactgga tgtcttgggt ccggcaagcc     120
ccagggaagg gactggtgtg ggtgagcgat attaatagtg acggctcttc tactaagtat     180
gctgatagtg tcaagggccg attccacatc tcacgagaca acgccaagaa caccttgtac     240
ctccagatga actctttgag agctgaggat acagcagtgt attactgtat cgcccactac     300
tcagggggag gctttgctta ctggggtcaa ggcacactcg tgacagtctc ctct           354

<210> SEQ ID NO 46
<211> LENGTH: 336
<212> TYPE: DNA
<213> ORGANISM: Artificial Sequence
<220> FEATURE:
<223> OTHER INFORMATION: VL  HzD-A10

<400> SEQUENCE: 46
gatattgtaa tgactcaagc tccactctcc ttgcctgtaa ctcctggaga gcccgcttct      60
attagctgta ggagtagtaa aagcctgctt acagtaatg gttacaatta cctgtactgg     120
tttttgcaga agcctggaca gtcaccccag ctcctcatct attatatgtc taacttggcc     180
agtggtgtcc cagaccgttt tagtggcagc ggctcaggca ccgactttac ccttaagatc     240
agccgagtcg aggctgaaga cgtaggagtg tactactgta tgcagagtct tgagtatcca     300
ttcaccttcg ggcagggcac caagctcgaa ataaag                                336

<210> SEQ ID NO 47
<211> LENGTH: 330
<212> TYPE: PRT
<213> ORGANISM: Artificial Sequence
<220> FEATURE:
<223> OTHER INFORMATION: CH of chD-A10

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 48
<211> LENGTH: 993
<212> TYPE: DNA
<213> ORGANISM: Artificial Sequence
<220> FEATURE:
<223> OTHER INFORMATION: CH of chD-A10

<400> SEQUENCE: 48
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtcgtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                  993
```

```
<210> SEQ ID NO 49
<211> LENGTH: 107
<212> TYPE: PRT
<213> ORGANISM: Artificial Sequence
<220> FEATURE:
<223> OTHER INFORMATION: CL of chD-A10

<400> SEQUENCE: 49

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 50
<211> LENGTH: 324
<212> TYPE: DNA
<213> ORGANISM: Artificial Sequence
<220> FEATURE:
<223> OTHER INFORMATION: CL of chD-A10

<400> SEQUENCE: 50
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct caatcgggt aactcccagg agagtgtcac agagcaggac      180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                            324
```

ANTI-CK8 ANTIBODIES FOR USE IN THE TREATMENT OF COLORECTAL CANCERS

FIELD OF THE INVENTION

The present invention relates to the field of antibodies that can be used for therapeutic purposes. In particular, the present invention relates to an anti-cytokeratin-8 antibody. These antibodies are useful in the treatment of cancers expressing cytokeratin-8 (CK8), for example colorectal cancers.

BACKGROUND OF THE INVENTION

Cytokeratin-8 (CK8) is a protein component of the intermediate filaments of the epithelial cell cytoskeleton.

Various studies have shown that CK8 protein is present associated to the plasma membrane of various cancer cells. For example, Godfroid et al. (Journal of Cell Science, 99: 595-607, 1991) described the presence of CK8 proteins on the surface of cultured breast cancer cells. Hembrough et al. (Journal of Cell Science, 108: 1071-1082, 1995) described the presence of CK8 or a CK8-like protein on the surface of hepatocytes, HepG2 cells and breast cancer cells.

CK8 protein has also been detected on the surface of carcinomas of other cancers, such as upper digestive tract cancer (Gires et al., Biochemical and Biophysical Research Communications, 328: 1154-1162, 2005). It has also been shown that CK8 protein is exposed on the surface of invasive and non-invasive tumor cells in colorectal cancers (WO2010/136536). More particularly, it has been shown that in colorectal cancers the appearance of invasive and/or metastatic cells is accompanied by cleavage of human CK8 protein exposed on the surface of these cells. The N-terminus portion of CK8 protein remains exposed on the surface of colon adenocarcinoma cells whereas the C-terminus portion of the protein partially or completely disappears from the surface of these cells.

Colorectal cancer is a particularly invasive cancer. Although significant improvements have been made in the treatment of metastatic colorectal cancer (CRC) patients, this type of cancer remains a significant global public health problem (Weitz et al. Lancet 2005; 365: 153-65). CRC is the third most diagnosed cancer in both sexes with an estimated 940,000 cases per year and the second most common cause of cancer deaths with about 500,000 cases per year (Weitz et al. Lancet 2005; 365: 153-65). In France, 37,000 new patients are diagnosed with CRC each year, of which about half will die of the metastatic disease. However, about 50% of the 36,000 new patients already have metastases at the time of diagnosis or will develop metastases (Weitz et al. Lancet 2005; 365: 153-65; Cunningham et al. Lancet 2010; Chevreul Eur J Health Econ 2010).

The development of more effective drugs (Irinotecan, Oxaliplatin) has made it possible to significantly improve treatments for CRC patients. The last decade has also seen the emergence of molecule-based therapies—monoclonal antibodies (Mab)—directed against specific targets overexpressed (EGF or VEGF receptors) in tumor cells relative to healthy cells. These molecules significantly improve treatments.

Cytokeratin 8 exhibits multiple functions, such as for example the modulation of cell invasion and/or cell apoptosis on the basis of its unique structural hallmark. Related to the cell invasion, CK8 binds plasminogen and tissue-type plasminogen activator (t-PA) and accelerates plasminogen activation on cancer cell surfaces (J Protein Chem. 1998 November; 17(8):845-54). The plasminogen-binding site is located at the C-terminus of CK8.

In addition, by interfering with the plasminogen system, CK8 could be involved in the modulation of the outside-in signal transduction of cancer cells in response to microenvironmental changes (Deryugina and Quigley, J. Biomed Biotechnol, 2012; 2012:564259).

Related to cell apoptosis, the cytokeratin 8/18 (CK8/18) cytoskeleton network is an early target for caspase cleavage during apoptosis. Recent reports suggest that the highly conserved and ubiquitous death effector domain containing DNA binding protein (DEDD) plays a role in the recruitment of procaspase-9 and -3 at this CK8/18 scaffold. DEDD interacts with both the CK8/18 intermediate filament network and procaspase-3 and procaspase-9, (Apoptosis (2006) 11:1561-1572). It is suggested that the CK8/18 fibrils may provide a scaffold for the proximity-induced auto cleavage and activation of procaspase-9 in close association with caspase-3.

Various monoclonal antibodies binding to human CK8 protein have been described. In particular, Erlandsson et al. (J. of Molecular Recognition, 16: 157-163, 2003; Johansson et al. Cancer Res 1999, 59, 48-51) described the monoclonal antibody TS1 directed against human CK8 protein, its anti-idiotype αTS1, and the use thereof in immunotherapy for treating carcinomas. Doljak et al. (Cancer Letters, 267: 75-84, 2008) described a monoclonal antibody binding to the VKIALEVEIATY motif conserved among various cytokeratins. This monoclonal antibody binds in particular to CK2, CK8, CK10 and CK18 proteins in MCF-7 breast cancer cells. This antibody inhibits activation of plasminogen on MCF-7 cells in vitro. The antibody M20 marketed by Sigma® was described by Van Muijen, G. et al. (Lab. Invest., 57: 359, 1987; Waseem et al. Biochemistry 2004, 43, 1283-1295). It has been shown that this antibody, specifically binding to CK8 protein, inhibits the growth and the invasive capacity of colorectal cancer tumor cells in tests conducted in vitro and in vivo (WO2010/136536). In particular, in the international patent application WO2010/136536, it was shown that this antibody specifically binds to the uncleaved portion of human CK8 protein present on the surface of colon adenocarcinoma tumor cells. The purified antibody M20 was produced by mouse ascitic fluid. No humanized Mab format has been described for this particular antibody.

Although progress has been made in the identification of antigens on the surface of tumor cells and in the understanding of the mechanisms associated with the development of cancers, and although this progress has enabled the development of monoclonal antibodies that can significantly improve treatments, the effectiveness and the specificity of said monoclonal antibodies can be further improved. Indeed many of the proteins used for the development of targeted therapies are over-expressed in cancer cells but are also expressed, albeit at different levels in healthy tissues. Therefore drugs targeting for a protein key epitope that is more specifically expressed at the cell surface in cancer tissue represent a very promising approach to improve the cancer specificity of the anti-cancer treatments. Thus, there remains a need to develop therapeutic means for treating tumors whose cells express externalized CK8 (eCK8) protein on their surface, in particular for treating colorectal cancers for example. More particularly, there remains a need to develop monoclonal antibodies not only targeting CK8 but more specifically targeting a cancer related epitope that interferes with the tumorigenesis capacities of the cells by modulating well described essential processes of tumor progression such as those involved in cell invasion and cell apoptosis.

BRIEF DESCRIPTION OF THE INVENTION

The present invention relates to an antibody, or antibody fragment thereof, specifically binding the peptide having the amino acid sequence of SEQ ID No. 29. The antibody comprises:
- a heavy chain comprising the following three CDRs, respectively CDR-H1, CDR-H2 and CDR-H3, wherein:
  - CDR-H1 comprises the sequence SEQ ID No. 37, or a sequence with at least 80%, preferably 85%, 90%, 95% and 98%, identity after optimal alignment with sequence SEQ ID No. 37; and
  - CDR-H2 comprises the sequence SEQ ID No. 38, or a sequence with at least 80%, preferably 85%, 90%, 95% and 98%, identity after optimal alignment with sequence SEQ ID No. 38; and
  - CDR-H3 comprises the sequence SEQ ID No. 39, or a sequence with at least 80%, preferably 85%, 90%, 95% and 98%, identity after optimal alignment with sequence SEQ ID No. 39; and
- a light chain comprising the following three CDRs, respectively CDR-L1, CDR-L2 and CDR-L3, wherein:
  - CDR-L1 comprises the sequence SEQ ID No. 34, or a sequence with at least 80%, preferably 85%, 90%, 95% and 98%, identity after optimal alignment with sequence SEQ ID No. 34; and
  - CDR-L2 comprises the sequence SEQ ID No. 35, or a sequence with at least 70%, preferably 80%, 85%, 90%, 95% and 98%, identity after optimal alignment with sequence SEQ ID No. 35; and
  - CDR-L3 comprises the sequence SEQ ID No. 36, or a sequence with at least 80%, preferably 85%, 90%, 95% and 98%, identity after optimal alignment with sequence SEQ ID No. 36.

The invention also relates to a humanized antibody, or antibody fragment thereof, specifically binding the peptide having the amino acid sequence of SEQ ID No. 29. The humanized antibody comprises:
- a heavy chain comprising the following three CDRs, respectively CDR-H1', CDR-H2' and CDR-H3', wherein:
  - CDR-H1' comprises the sequence SEQ ID No. 40, or a sequence with at least 80%, preferably 85%, 90%, 95% and 98%, identity after optimal alignment with sequence SEQ ID No. 37; and
  - CDR-H2' comprises the sequence SEQ ID No. 41, or a sequence with at least 80%, preferably 85%, 90%, 95% and 98%, identity after optimal alignment with sequence SEQ ID No. 38; and
  - CDR-H3' comprises the sequence SEQ ID No. 39, or a sequence with at least 80%, preferably 85%, 90%, 95% and 98%, identity after optimal alignment with sequence SEQ ID No. 39; and
- a light chain comprising the following three CDRs, respectively CDR-L1', CDR-L2' and CDR-L3', wherein:
  - CDR-L1' comprises the sequence SEQ ID No. 42, or a sequence with at least 80%, preferably 85%, 90%, 95% and 98%, identity after optimal alignment with sequence SEQ ID No. 34; and
  - CDR-L2' comprises the sequence SEQ ID No. 35, or a sequence with at least 70%, preferably 80%, 85%, 90%, 95% and 98%, identity after optimal alignment with sequence SEQ ID No. 35; and
  - CDR-L3' comprises the sequence SEQ ID No. 36, or a sequence with at least 80%, preferably 85%, 90%, 95% and 98%, identity after optimal alignment with sequence SEQ ID No. 36.

The antibody or antibody fragment of the present invention may be used for the treatment of tumors whose cells express CK8 protein, in particular the peptide of sequence according to SEQ ID No.29, on their surface.

The present invention also relates to a human CK8 antigen peptide consisting of a polypeptide having from 8 to 16 amino acids and comprising the sequence of SEQ ID No. 29, in particular to a human CK8 antigen peptide consisting of the sequence of SEQ ID No. 29.

The present invention also relates to said human CK8 antigen peptide for its use as a medicament.

The present invention also relates to a pharmaceutical composition comprising an antibody or antibody fragment according to the present invention and a suitable pharmaceutical carrier, in particular for its use in the treatment or the prevention of a cancer, an autoimmune disease, an inflammatory condition, a viral infection or a viral disease and/or as a medicament to induce apoptosis of a tumor cell, in particular for use in the treatment of tumors whose cells express CK8 protein, in particular the peptide of sequence according to SEQ ID No.29, on their surface.

Lastly, the present invention relates to a kit comprising a container containing a molecule that can bind to an epitope, wherein said epitope has a sequence with at least 60%, preferably 65%, 70%, 75%, 80%, 85%, 90%, and 100%, identity after optimal alignment with sequence SEQ ID No. 29. Said kit can be used for detecting cancer.

BRIEF DESCRIPTION OF THE DRAWINGS

FIGS. 1A and 1B illustrate the detection by Western Blot of CK8 isoforms using different anti-CK8 antibodies including the mD-A10 Mab.

FIGS. 2A and 2B illustrate the level of competition in the presence of unconjugated peptide 1 (SEQ ID NO: 1) or unconjugated peptide 2 (SEQ ID NO: 2) on the cell labeling of anti-CK8 antibodies analyzed by flow cytometry.

FIGS. 3A, B and C illustrate the level of competition in the presence of unconjugated peptide 1 (SEQ ID NO: 1) or unconjugated peptide 2 (SEQ ID NO: 2) on the detection of CK8 protein isoforms by Western Blot using the M20 antibody, the mD-D6 Mab or the mD-A10 Mab.

FIG. 11 illustrates the positioning of peptides 1 (SEQ ID NO: 1), 2 (SEQ ID NO: 2), 3 (SEQ ID NO: 3) and 4 (SEQ ID NO: 4) in the human cytokeratin-8 sequence (ref.: Uni-ProtKB P05787).

FIG. 17 illustrates the amino acid and nucleic acid sequences of the heavy chain variable (VH) region of the mD-A10 Mab with descriptions of FR1, CDR1, FR2, CDR2, FR3 and CDR3 according to IMGT®.

FIG. 18 illustrates the amino acid and nucleic acid sequences of the heavy chain variable (VH) region of the humanized monoclonal antibody derivate of the mD-A10 Mab.

FIG. 20 illustrates the amino acid and nucleic acid sequences of the heavy chain constant (CH) region of the humanized monoclonal antibody derivate of the mD-A10 Mab.

FIG. 21 illustrates the amino acid and nucleic acid sequences of the light chain constant (CL) region of the humanized monoclonal antibody derivate of the mD-A10 Mab.

DEFINITIONS

Figure 4:
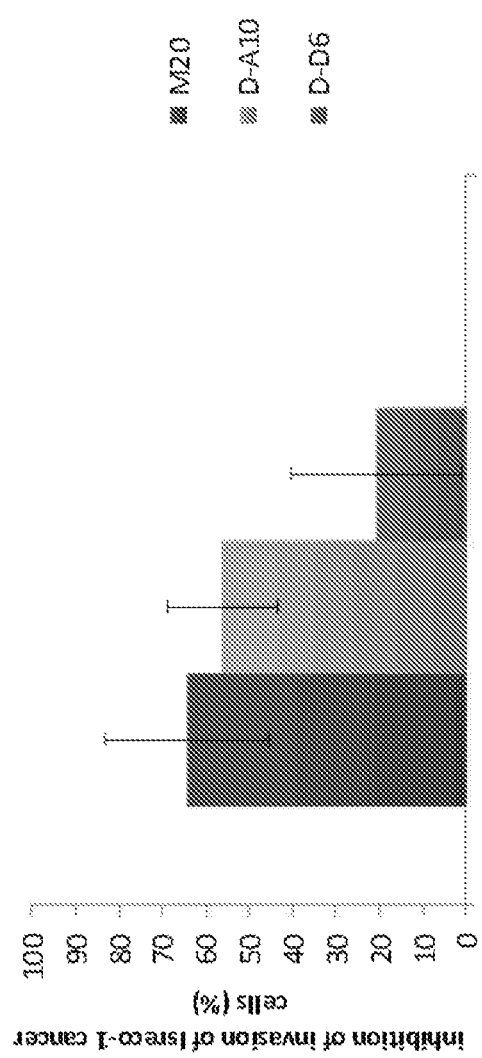
FIG. 4 illustrates the effect of anti-CK8 antibodies (50 µg/ml) including the mD-A10 Mab on the invasion of Isreco-1 cells induced by 10% fetal bovine serum (FBS).

The term "antibodies" as used in the description of the present invention refers to monoclonal antibodies (Mabs) or polyclonal antibodies. The antibodies may be chimeric, humanized or conjugated antibodies. A typical antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions are called the "framework regions".

The expression "monoclonal antibodies" as used in the description of the present invention refers to an antibody arising from a population of substantially homogeneous antibodies. More particularly, the individual antibodies of a population are identical except for a few possible naturally-occurring mutations which may be found in minimal amounts. In other words, a monoclonal antibody consists of a homogeneous antibody resulting from the proliferation of a single cell clone (for example a hybridoma, a eukaryotic host cell transfected with a DNA molecule encoding the homogeneous antibody, a prokaryotic host cell transfected with a DNA molecule encoding the homogeneous antibody, etc.) generally characterized by heavy chains of a single class and subclass and light chains of a single type. Monoclonal antibodies are highly specific and are directed against a single antigen. Moreover, unlike polyclonal antibody preparations that typically comprise various antibodies directed against various determinants or epitopes, each monoclonal antibody is directed against a single epitope of the antigen.

The expression "chimeric antibodies" as used in the description of the present invention refers to antibodies comprising the constant portions of the heavy and light chains of an antibody of a given species, for example a human antibody, on which are grafted the variable portions of the heavy and light chains of an antibody of a heterologous species, for example a murine antibody.

The expression "humanized antibodies" as used in the description of the present invention refers to human antibodies in which the hypervariable regions (CDRs) are replaced with the hypervariable regions (CDRs) of an antibody of heterogeneous origin, for example of murine origin, which constitute the antigen binding site. Since certain amino acids located in regions adjacent to CDRs (FRs) play a role in the structure of the antigen binding site, human antibodies may in addition be modified (CDR) so as to include amino acids of the FR of the antibody of heterogeneous origin.

The expression "conjugated antibodies" as used in the description of the present invention refers to artificial mixed molecules in which the components are associated with an antibody capable of selectively recognizing an antigen. These components may be cytotoxic drugs, anticancer agents, toxins, fragments and/or radioelements.

The antibodies may be multivalent antibodies, i.e. they may comprise more than two antigen binding sites or be multi-specific antibodies as long as they exhibit the desired biological activity.

The expression "antibody fragment(s)" as used in the description of the present invention refers to functional portions of antibodies (as opposed to the whole antibodies), that is, portions of the antibodies able to bind to an antigen (antigen binding fragment). It is to be understood that the antibody fragments retain the ability to bind to the target (also generally referred to as antigen) of the antibody of reference. Examples of antibody fragments include the following fragments: Fv (composed of the variable regions of the heavy and light chains of an antibody), ScFv (divalent single-chain variable fragment), Fab (composed of the entire light chain and part of the heavy chain), F(ab')2 (composed of two Fab fragments linked by the hinge region), or any fragment whose half-life would be increased by chemical modification, such as the addition of poly(alkylene) glycol such as poly(ethylene) glycol ("PEGylation") (pegylated fragments called Fv-PEG, scFv-PEG, Fab-PEG, F(ab')2-PEG or Fab'-PEG) ("PEG" for Poly(Ethylene) Glycol), or by incorporation in a liposome, said fragments having at least one of the characteristic CDRs of the antibody according to the invention. Typically, an antibody fragment can have any upper size limit so long as it is similar or has immunological properties relative to antibody that binds with specificity to an epitope of the antibody of reference. For example, binding entities and light chain antibody fragments can have at least 60 amino acids, less than about 200 amino acids, less than about 175 amino acids, less than about 150 amino acids, or less than about 120 amino acids if the antibody fragment is related to a light antibody subunit. Moreover, binding entities and heavy chain antibody fragments can have less than about 425 amino acids, less than, about 400 amino acids, less than about 375 amino acids, less than about 350 amino acids, less than about 325 amino acids or less than about 300 amino acids if the antibody fragment is related to a heavy chain antibody subunit.

The term "apoptosis" as used in the description of the present invention refers to orderly or controlled form of cell death in mammals that is typically accompanied by one or more characteristic cell changes, such as condensation of cytoplasm, loss of plasma membrane microvilli, segmentation of the nucleus, degradation of chromosomal DNA or loss of mitochondrial function. Activation of cysteine proteases called caspases plays a major role in the execution of apoptosis.

The term "invasion" as used in the description of the present invention refers to cell migration, and defines the ability of cells to become motile and to navigate through the extracellular matrix within a tissue or to infiltrate neighboring tissues. Cancer cells that become invasive may disseminate to secondary sites and form metastases.

The term "agonist" or "agonistic" as used in the description of the present invention refers to a molecule which is capable of, directly or indirectly, inducing, promoting or enhancing CK8 biological activity or activation.

The terms "antagonist" or "antagonistic" as used in the description of the present invention refers to a molecule which is capable of, directly or indirectly, counteracting, reducing or inhibiting CK8 biological activity or activation.

The term "cancer" as used in the description of the present invention refers to all malignant neoplastic formations whatever their histological nature. There are two main categories of malignant tumors: carcinomas of epithelial origin and sarcomas of conjunctive origin. Malignant tumors are composed of invasive or spreading atypical cells characterized generally by an ability to grow autonomously, an imprecise delineation, an ability to invade neighboring tissues and vessels and a tendency to spread through the production of metastases.

The term "polynucleotide" as used in the description of the present invention refers to a single-stranded DNA or RNA nucleotide chain or its complement, or to a double-stranded complementary DNA (cDNA) or genomic DNA nucleotide chain.

The term "epitope" as used in the description of the present invention refers to a molecule that can be recognized by a paratope (variable portion of an antibody).

The term "homology" as used in the present description refers to the similarity between peptide sequences. The peptide sequences may have a deletion, an addition or a substitution of at least one amino acid compared with the reference polypeptide.

The "percentage identity" between two nucleic acid or amino acid sequences as used in the description of the present invention is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences. For example, the BLAST program, "BLAST 2 sequences" (Tatusova et al., "Blast 2 sequences—a new tool for comparing protein and nucleotide sequences", FEMS Microbiol., 1999, Lett. 174: 247-250) available on the site http://www.ncbi.nlm.nih.gov/gorf/b12.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

Murine monoclonal antibody D-A10 is referred to herein as "mD-A10 Mab".

Chimeric monoclonal antibody D-A10 is referred to herein as "chD-A10 Mab".

Humanized monoclonal antibody D-A10 is referred to herein as "HzD-A10 Mab".

SEQUENCE LISTING

SEQ ID NO: 1 refers to the following peptide:
AEQRGELAIKDANAKLSELEAALQRAKQD-C

SEQ ID NO: 2 refers to the following peptide:
AEQRGELAIKDANAKLSELE-C

SEQ ID NO: 3 refers to the following peptide:
AALQRAKQD-C

SEQ ID NO: 4 refers to the following peptide:
SELEAALQRAKQD-C

SEQ ID NO: 5 refers to the following peptide:
AEQRGELAIKDANAKLSELEAALQRAKQD

SEQ ID NO: 6 refers to the following peptide:
AALQRAKQD

SEQ ID NO: 7 refers to the following peptide:
EAALQRAKQD

SEQ ID NO: 8 refers to the following peptide:
LEAALQRAKQD

SEQ ID NO: 9 refers to the following peptide:
ELEAALQRAKQD

SEQ ID NO: 10 refers to the following peptide:
SELEAALQRAKQD

SEQ ID NO: 11 refers to the following peptide:
LSELEAALQRAKQD

SEQ ID NO: 12 refers to the following peptide:
KLSELEAALQRAKQD

SEQ ID NO: 13 refers to the following peptide:
AKLSELEAALQRAKQD

SEQ ID NO: 14 refers to the following peptide:
NAKLSELEAALQRAKQD

SEQ ID NO: 15 refers to the following peptide:
ANAKLSELEAALQRAKQD

SEQ ID NO: 16 refers to the following peptide:
DANAKLSELEAALQRAKQD

SEQ ID NO: 17 refers to the following peptide:
C-AIKDANAKLSELEAALQRAKQD

SEQUENCE LISTING

SEQ ID NO: 18 refers to the following peptide:
AIKDANAKLSELEAALQRAKQ

SEQ ID NO: 19 refers to the following peptide:
AIKDANAKLSELEAALQRAK

SEQ ID NO: 20 refers to the following peptide:
AIKDANAKLSELEAALQRA

SEQ ID NO: 21 refers to the following peptide:
AIKDANAKLSELEAALQR

SEQ ID NO: 22 refers to the following peptide:
AIKDANAKLSELEAALQ

SEQ ID NO: 23 refers to the following peptide:
AIKDANAKLSELEAAL

SEQ ID NO: 24 refers to the following peptide:
AIKDANAKLSELEAA

SEQ ID NO: 25 refers to the following peptide:
AIKDANAKLSELEA

SEQ ID NO: 26 refers to the following peptide:
AIKDANAKLSELE

SEQ ID NO: 27 refers to the following peptide:
AIKDANAKLSEL

SEQ ID NO: 28 refers to the following peptide:
AIKDANAKLSE

SEQ ID NO: 29 refers to the following peptide:
LSELEAAL

SEQ ID NO: 30 refers to the following nucleotide sequence:
AACATTGTTATGACCCAGGCCGCACCCTCTGTACCTGTCACTCCTGGAG
AGTCAGTATCCATCTCCTGCAGGTCTAGTAAGAGTCTTCTGTATAGTAA
TGGCAACACTTATTTGTATTGGTTCCTGCAGAGGCCAGGCCAGTCTCCT
CAGCGCCTGATATATTATATGTCCAACCTTGCCTCAGGAGTCCCAGACA
GGTTCAGTGGCAGAGGGTCAGGAACTGATTTCACACTGAGAATCAGTAG
AGTGGAGGCTGAGGATGTGGGTGTTTATTACTGTATGCAAAGTCTAGAA
TATCCTTTCACG SEQ ID NO: 31 refers to the following peptide:
NIVMTQAAPSVPVTPGESVSISCRSSKSLLYSNGNTYLYWFLQRPGQSP
QRLIYYMSNLASGVPDRFSGRGSGTDFTLRISRVEAEDVGVYYCMQSLE
YPFTFGGGTKLEIK SEQ ID NO: 32 refers to the following nucleotide sequence:
GAAGTGCAGCTGTTGGAGACTGGAGGAGGCTTGGTGCAACCGGGGGGT
CACGGGGACTCTCTTGTGAAGGCTCAGGGTTTACTTTTAGTGGCTTCTG
GATGAGCTGGGTTCGACAGACACCTGGGAAGACCCTGGAGTGGATTGGA
GACATTAATTCTGATGGCAGTGCAATAAAATACGCACCATCCATAAAGG
ATCGATTCACTATCTTCAGAGACAATGACAAGAGCACCCTGTACCTGCA
GATGAGCAATGTGCGATCTGAGGACACAGCCACGTATTTCTGTATCGCC
CATTACTCCGGTGGGGGGTTTGCTTACTGGGGTCAAGGAACCTCGGTCA
CCGTCTCCTCA SEQ ID NO: 33 refers to the following peptide:
EVQLLETGGGLVQPGGSRGLSCEGSGFTFSGFWMSWVRQTPGKTLEWIG
DINSDGSAIKYAPSIKDRFTIFRDNDKSTLYLQMSNVRSEDTATYFCIA
HYSGGGFAYWGQGTSVTVSS SEQ ID NO: 34 refers to the following peptide:
KSLLYSNGNTY SEQ ID NO: 35 refers to the following peptide:
YMS SEQ ID NO: 36 refers to the following peptide:
MQSLEYPFT SEQ ID NO: 37 refers to the following peptide:
GFTFSGFW SEQ ID NO: 38 refers to the following peptide:
INSDGSAI SEQ ID NO: 39 refers to the following peptide:
IAHYSGGGFAY SEQ ID NO: 40 refers to the following peptide:
GFTFSSYW SEQ ID NO: 41 refers to the following peptide:
INSDGSST SEQ ID NO: 42 refers to the following peptide:
KSLLYSNGYNY SEQ ID NO: 43 refers to the following peptide:
DIVMTQAPLSLPVTPGEPASISCRSSKSLLYSNGYNYLYWFLQKPGQSP
QLLIYYMSNLASGVPDRFSGSGSGTDFTLKISRVEAEDVGVYYCMQSLE
YPFTFGQGTKLEIK SEQ ID NO: 44 refers to the following peptide:
EVQLVESGGGLVQPGGSLRLSCAASGFTFSSYWMSWVRQAPGKGLVWVS
DINSDGSSTKYADSVKGRFTISRDNAKNTLYLQMNSLRAEDTAVYYCIA
HYSGGGFAYWGQGTLVTVSS SEQ ID NO: 45 refers to the following nucleotide sequence:
GAAGTACAATTGGTAGAATCAGGTGGTGGTTTGGTTCAGCCAGGAGGAT
CACTGAGACTGTCCTGCGCTGCAAGCGGCTTTACCTTCTCTAGCTACTG
GATGTCTTGGGTCCGGCAAGCCCCAGGGAAGGGACTGGTGTGGGTGAGC
GATATTAATAGTGACGGCTCTTCTACTAAGTATGCTGATAGTGTCAAGG
GCCGATTCACCATCTCACGAGACAACGCCAAGAACACCTTGTACCTCCA
GATGAACTCTTTGAGAGCTGAGGATACAGCAGTGTATTACTGTATCGCC
CACTACTCAGGGGGAGGCTTTGCTTACTGGGGTCAAGGCACACTCGTGA
CAGTCTCCTCT SEQ ID NO: 46 refers to the following nucleotide sequence:
GATATTGTAATGACTCAAGCTCCACTCTCCTTGCCTGTAACTCCTGGAG
AGCCCGCTTCTATTAGCTGTAGGAGTAGTAAAAGCCTGCTTTACAGTAA
TGGTTACAATTACCTGTACTGGTTTTTGCAGAAGCCTGGACAGTCACCC
CAGCTCCTCATCTATTATATGTCTAACTTGGCCAGTGGTGTCCCAGACA
GTTTTAGTGGCAGCGGCTCAGGCACCGACTTTACCCTTAAGATCAGCCG
AGTCGAGGCTGAAGACGTAGGAGTGTACTACTGTATGCAGAGTCTTGAG
TATCCATTCACCTTCGGGCAGGGCACCAAGCTCGAAATAAAG SEQ ID NO: 47 refers to the following peptide:
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK SEQ ID NO: 48 refers to the following nucleotide sequence:
GCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTT
CCCCGAACCGGTGACGGTGTCGTGGAACTCAGGCGCCCTGACCAGCGGC
GTGCACACCTTCCCGGCTGTCCTACAGTCCTCAGGACTCTACTCCCTCA
GCAGCGTCGTGACCGTGCCCTCCAGCAGCTTGGGCACCCAGACCTACAT
CTGCAACGTGAATCACAAGCCCAGCAACACCAAGGTGGACAAGAAAGTT
GAGCCCAAATCTTGTGACAAAACTCACACATGCCCACCGTGCCCAGCAC
CTGAACTCCTGGGGGGACCGTCAGTCTTCCTCTTCCCCCCAAAACCCAA
GGACACCCTCATGATCTCCCGGACCCCTGAGGTCACATGCGTGGTGGTG
GACGTGAGCCACGAAGACCCTGAGGTCAAGTTCAACTGGTACGTGGACG
GCGTGGAGGTGCATAATGCCAAGACAAAGCCGCGGGAGGAGCAGTACAA
CAGCACGTACCGTGTGGTCAGCGTCCTCACCGTCCTGCACCAGGACTGG
CTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACC
ACAGGTGTACACCCTGCCCCCATCCCGGGATGAGCTGACCAAGAACCAG
GTCAGCCTGACCTGCCTGGTCAAAGGCTTCTATCCCAGCGACATCGCCG
TGGAGTGGGAGAGCAATGGGCAGCCGGAGAACAACTACAAGACCACGCC -continued

SEQUENCE LISTING

```
TCCCGTGCTGGACTCCGACGGCTCCTTCTTCCTCTACAGCAAGCTCACC
GTGGACAAGAGCAGGTGGCAGCAGGGGAACGTCTTCTCATGCTCCGTGA
TGCATGAGGCTCTGCACAACCACTACACGCAGAAGAGCCTCTCCCTGTC
TCCGGGTAAATGA

SEQ ID NO: 49 refers to the following peptide:
RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC SEQ ID NO: 50 refers to the following nucleotide
sequence:
CGAACTGTGGCTGCACCATCTGTCTTCATCTTCCCGCCATCTGATGAGC
AGTTGAAATCTGGAACTGCCTCTGTTGTGTGCCTGCTGAATAACTTCTA
TCCCAGAGAGGCCAAAGTACAGTGGAAGGTGGATAACGCCCTCCAATCG
GGTAACTCCCAGGAGAGTGTCACAGAGCAGGACAGCAAGGACAGCACCT
ACAGCCTCAGCAGCACCCTGACGCTGAGCAAAGCAGACTACGAGAAACA
CAAAGTCTACGCCTGCGAAGTCACCCATCAGGGCCTGAGCTCGCCCGTC
ACAAAGAGCTTCAACAGGGGAGAGTGTTAG
```

DETAILED DESCRIPTION OF THE INVENTION

Antibodies and Antibody Fragments

The Inventors have developed antibodies and antibody fragments that specifically bind to the peptide having the amino acid sequence from position 353 to position 360 of human CK8 protein (ref.: Uni-ProtKB P05787). The amino acid sequence from position 353 to position 360 of human CK8 protein is presented in SEQ ID NO: 29. By "specifically" it is meant that the antibodies or antibody fragments only bind to the human CK8 peptide having said sequence.

It is understood that the antibodies or antibody fragments can bind to any protein/peptide fragment comprising said sequence.

The present invention thus relates to antibodies, or antibody fragments thereof, specifically binding to the peptide according to sequence SEQ ID NO: 29. These antibodies or antibody fragments are designated in the description of the present invention by the expression "antibodies or antibody fragments of the present invention."

The antibodies of the present invention comprise:
a heavy chain comprising the following three CDRs, respectively CDR-H1, CDR-H2 and CDR-H3, wherein:

CDR-H1 comprises the sequence SEQ ID No. 37, or a sequence with at least 80%, preferably 85%, 90%, 95% and 98%, identity after optimal alignment with sequence SEQ ID No. 37; and CDR-H2 comprises the sequence SEQ ID No. 38, or a sequence with at least 80%, preferably 85%, 90%, 95% and 98%, identity after optimal alignment with sequence SEQ ID No. 38; and CDR-H3 comprises the sequence SEQ ID No. 39, or a sequence with at least 80%, preferably 85%, 90%, 95% and 98%, identity after optimal alignment with sequence SEQ ID No. 39; and a light chain comprising the following three CDRs, respectively CDR-L1, CDR-L2 and CDR-L3, wherein:

CDR-L1 comprises the sequence SEQ ID No. 34, or a sequence with at least 80%, preferably 85%, 90%, 95% and 98%, identity after optimal alignment with sequence SEQ ID No. 34; and CDR-L2 comprises the sequence SEQ ID No. 35, or a sequence with at least 70%, preferably 80%, 85%, 90%, 95% and 98%, identity after optimal alignment with sequence SEQ ID No. 35; and CDR-L3 comprises the sequence SEQ ID No. 36, or a sequence with at least 80%, preferably 85%, 90%, 95% and 98%, identity after optimal alignment with sequence SEQ ID No. 36.

The CDR sequences are defined in accordance with IMGT®, Kabat® or the common numbering system which retains sequences common to IMGT® and Kabat® (see Examples section). The CDRs of the antibodies of the present invention, in particular of the mD-A10 Mab, are presented in Table 1.

TABLE 1

CDR sequences for VH or VL of the mD-A10 Mab

| | SEQ ID NO: | IMGT ® sequence | SEQ ID NO: | Kabat ® sequence | SEQ ID NO: | Sequence (Common numbering system) |
|---|---|---|---|---|---|---|
| | | | VL mD-A10 | | | |
| CDR1 | 34 | KSLLYSNGNTY | 34K | RSSKSLLYSNGNTYLY | 34C | KSLLYSNGNTY |
| CDR2 | 35 | YMS | 35K | YMSNLAS | 35C | YMS |
| CDR3 | 36 | MQSLEYPFT | 36K | MQSLEYPFT | 36C | MQSLEYPFT |
| | | | VH mD-A10 | | | |
| CDR1 | 37 | GFTFSGFW | 37K | GFWMS | 37C | GFW |
| CDR2 | 38 | INSDGSAI | 38K | DINSDGSAIKYAPSIKD | 38C | INSDGSAI |
| CDR3 | 39 | IAHYSGGGFAY | 39K | HYSGGGFAY | 39C | HYSGGGFAY |

By definition, these CDRs comprise variant CDRs arising by deletion, substitution or addition of one or more amino acids, said variant retaining the specificity of the original CDR. The common numbering system provides a CDR definition having short amino acid sequences or the definition of the minimum CDR.

The antibodies or antibody fragments of the present invention (anti-CK8 antibodies or anti-CK8 antibody fragments) efficiently inhibit the invasive capacity of tumor cells in vitro and effectively inhibit tumor growth in vivo.

The antibodies or antibody fragments of the present invention (anti-CK8 antibodies or anti-CK8 antibody fragments) efficiently induce the death of CK8-expressing cancer cells in vivo via Caspase 3 mediated apoptosis. Indeed, the antibodies or antibody fragments of the present invention are able to induce in vivo cleavage of caspase 3, which evidences activation of apoptosis.

The antibodies of the present invention are preferably monoclonal antibodies. Said monoclonal antibodies may be murine, chimeric or humanized antibodies. They may be obtained by standard methods well-known to the person skilled in the art.

Monoclonal antibodies, in particular of murine origin, can be prepared according to the techniques described in the manual *Antibodies* (Harlow and Lane, Antibodies: A Laboratory Manual, Cold Spring Harbor Laboratory, Cold Spring Harbor N.Y., pp. 726, 1988) or prepared from hybridomas. Such techniques are well-known to the person skilled in the art.

Alternatively, the monoclonal antibodies of the present invention can be obtained, for example, from cells of an animal immunized with a human CK8 protein fragment comprising the peptide having SEQ ID NO: 1 or SEQ ID NO: 2 and then screening of monoclonal antibodies binding to peptide having SEQ ID NO: 29 by epitope mapping.

The monoclonal antibodies according to the invention can, for example, be purified on an affinity column on which has been immobilized beforehand a human CK8 fragment comprising the peptide of SEQ ID NO: 29. Other purification techniques well-known to the person skilled in the art may be used simultaneously or successively.

Chimeric antibodies can be prepared using genetic recombination techniques. For example, the chimeric antibody can be produced by cloning a recombinant DNA having a promoter and a sequence encoding the variable region of a nonhuman, in particular murine monoclonal antibody and a sequence encoding the constant region of the human antibody. A chimeric antibody of the invention encoded by such a recombinant gene will be, for example, a mouse-human chimera, the specificity of this antibody being determined by the variable region derived from the murine DNA and its isotype being determined by the constant region derived from the human DNA. Methods for producing chimeric antibodies are extensively described in the literature.

Humanized antibodies can be prepared by techniques known to a person skilled in the art (such as, for example, those described in Singer et al., J. Immun., 150:2844-2857, 1992; Mountain et al., Biotechnol. Genet. Eng. Rev., 10:1-142, 1992; and Bebbington et al., Bio/Technology, 10:169-175, 1992). Other humanization techniques, also known to a person skilled in the art, such as, for example, the "CDR grafting" technique described in patents EP 0 451 261, EP 0 682 040, EP 0 939 127, EP 0 566 647 or U.S. Pat. Nos. 5,530,101, 6,180,370, 5,585,089 and 5,693,761, 5,639,641 or U.S. Pat. Nos. 6,054,297, 5,886,152 and 5,877,293 can also be cited.

To minimize anti-V region responses, monoclonal humanized antibodies may be prepared by grafting onto the human templates only the specificity-determining residues (SDRs), i.e. the residues that are essential for the surface complementarity of the Mab and its antigen. To that end, murine antibodies may be humanized by grafting their complementarity determining regions (CDRs) onto the variable light (VL) and variable heavy (VH) frameworks of human immunoglobulin molecules, while retaining those murine framework residues deemed essential for the integrity of the antigen-combining site. However, as the xenogeneic CDRs of the humanized antibodies may evoke anti-idiotypic (anti-Id) response in patients, the humanized antibodies of the invention or fragments thereof can be prepared by techniques minimizing the anti-Id response. Examples of these techniques include the grafting, onto the human frameworks, of only the specificity determining residues (SDRs), i.e. the CDR residues that are most crucial in the antibody-ligand interaction. The SDRs are identified through the help of the database of the three-dimensional structures of the antigen-antibody complexes of known structures or by mutational analysis of the antibody-combining site. An alternative approach to humanization, which involves retention of more CDR residues, is based on grafting of the 'abbreviated' CDRs, i.e. the stretches of CDR residues that include all the SDRs.

The antibody fragments of the present invention can be obtained from the antibodies herein described by enzymatic digestion, for example by means of pepsin or papain, and/or by cleavage of disulfide bridges by chemical reduction. Alternatively, the antibody fragments of the present invention can be obtained by gene recombination techniques or by peptide synthesis. These methods are well-known to the person skilled in the art.

The antibodies or antibody fragments of the present invention are preferably antibodies or antibody fragments selected from murine, chimeric and humanized antibodies, preferably having an optimized sequence.

The expression "optimized sequence" means in particular that the codons encoding the constitutive amino acids of the protein of interest (antibody variable domains, for example) can be optimized for better recognition by the translation machinery in a dedicated cell type. In this regard, the amino acid sequence of the protein encoded by the optimized sequence is identical to the non-optimized sequence, but the nucleotide sequence is different.

The antibodies of the present invention, or antibody fragments thereof, may comprise SEQ ID NO: 31 or a sequence with at least 80%, preferably 85%, 90%, 95% and 98%, identity after optimal alignment with sequence SEQ ID No. 31 and/or SEQ ID NO: 33 or a sequence with at least 80%, preferably 85%, 90%, 95% and 98%, identity after optimal alignment with sequence SEQ ID No. 33.

The antibodies of the present invention, or antibody fragments thereof, may comprise variable regions encoded by polynucleotides having the nucleotide sequence of the murine light-chain variable region (SEQ ID NO: 30) or a sequence with at least 80%, preferably 85%, 90%, 95% and 98%, identity after optimal alignment with sequence SEQ ID No. 30 and/or the nucleotide sequence of the murine heavy-chain variable region (SEQ ID NO: 32) or a sequence with at least 80%, preferably 85%, 90%, 95% and 98%, identity after optimal alignment with sequence SEQ ID No. 32.

Figure 16:
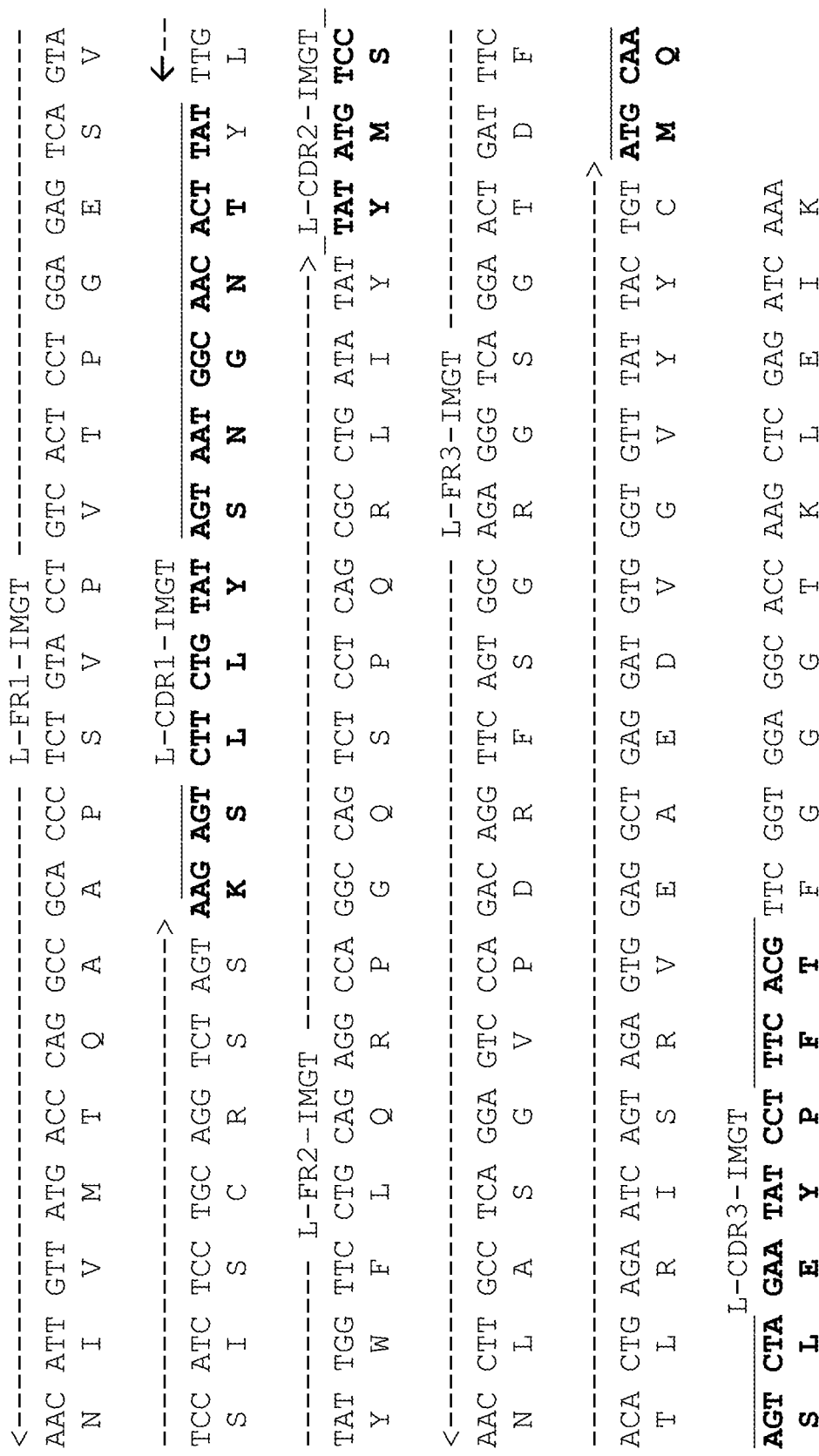
FIG. 16 illustrates the amino acid and nucleic acid sequences of the light chain variable (VL) region of the mD-A10 Mab with the description of FR1, CDR1, FR2, CDR2, FR3 and CDR3 according to IMGT®.

SEQ ID NO: 30 corresponds to the nucleotide sequence of the murine light-chain variable region of an antibody according to the present invention (mD-A10 Mab with descriptions of FR1, CDR1, FR2, CDR2, FR3 and CDR3 according to IMGT® presented in FIG. 16).

SEQ ID NO: 31 corresponds to the amino acid sequence of the murine light-chain variable region of an antibody according to the present invention (mD-A10 Mab with descriptions of FR1, CDR1, FR2, CDR2, FR3 and CDR3 according to IMGT® presented in FIG. 16).

SEQ ID NO: 32 corresponds to the nucleotide sequence of the murine heavy-chain variable region of an antibody according to the present invention (mD-A10 Mab with descriptions of FR1, CDR1, FR2, CDR2, FR3 and CDR3 according to IMGT® presented in FIG. 17).

SEQ ID NO: 33 corresponds to the amino acid sequence of the murine heavy-chain variable region of an antibody according to the present invention (mD-A10 Mab with descriptions of FR1, CDR1, FR2, CDR2, FR3 and CDR3 according to IMGT® presented in FIG. 17).

In some embodiments, the antibody of the present invention is the mD-A10 Mab.

The amino acid and nucleic acid sequences of the light-chain and heavy-chain variable regions of the mD-A10 Mab are presented in Table 2.

TABLE 2

Sequence codifications for CDR VH and CDR VL

|  | mVL nucleic acid sequence | mVH nucleic acid sequence |
|---|---|---|
| D-A10 | SEQ ID NO: 30 | SEQ ID NO: 32 |
|  | mVL amino acid sequence | mVH amino acid sequence |
| D-A10 | SEQ ID NO: 31 | SEQ ID NO: 33 |

The antibodies or antibody fragments of the present invention are preferably humanized antibodies or humanized antibody fragments.

The humanized antibodies of the present invention may comprise:

a heavy chain comprising the following three CDRs, respectively CDR-H1', CDR-H2' and CDR-H3', wherein:

CDR-H1' comprises the sequence SEQ ID No. 40, or a sequence with at least 80%, preferably 85%, 90%, 95% and 98%, identity after optimal alignment with sequence SEQ ID No. 40; and CDR-H2' comprises the sequence SEQ ID No. 41, or a sequence with at least 80%, preferably 85%, 90%, 95% and 98%, identity after optimal alignment with sequence SEQ ID No. 41; and CDR-H3' comprises the sequence SEQ ID No. 39, or a sequence with at least 80%, preferably 85%, 90%, 95% and 98%, identity after optimal alignment with sequence SEQ ID No. 39; and a light chain comprising the following three CDRs, respectively CDR-L1', CDR-L2' and CDR-L3', wherein:

CDR-L1' comprises the sequence SEQ ID No. 42, or a sequence with at least 80%, preferably 85%, 90%, 95% and 98%, identity after optimal alignment with sequence SEQ ID No. 42; and CDR-L'2 comprises the sequence SEQ ID No. 35, or a sequence with at least 70%, preferably 80%, 85%, 90%, 95% and 98%, identity after optimal alignment with sequence SEQ ID No. 35; and CDR-L'3 comprises the sequence SEQ ID No. 36, or a sequence with at least 80%, preferably 85%, 90%, 95% and 98%, identity after optimal alignment with sequence SEQ ID No. 36.

The CDR sequences of humanized antibodies of the present invention, in particular of Hz-DA-10 Mab, are summarized in Table 3 herein below.

TABLE 3

CDR sequences for VH and VL of Hz DA-10 Mab

|  | SEQ ID NO: | Sequence IMGT® | SEQ ID NO: | Sequence Kabat® | SEQ ID NO: | Sequence (Common numbering system) |
|---|---|---|---|---|---|---|
| Hz VH D-A10 | | | | | | |
| CDR1 | 40 | GFTFSSYW | 40K | SYWMS | 40C | SYW |
| CDR2 | 41 | INSDGSST | 41K | DINSDGSSTKYAPSIKD | 41C | INSDGSST |
| CDR3 | 39 | IAHYSGGGFAY | 39K | HYSGGGFAY | 39C | HYSGGGFAY |
| Hz VL D-A10 | | | | | | |
| CDR1 | 42 | KSLLYSNGYNY | 42K | RSSKSLLYSNGYNYLY | 42C | KSLLYSNGYNY |
| CDR2 | 35 | YMS | 35K | YMSNLAS | 35C | YMS |
| CDR3 | 36 | MQSLEYPFT | 36K | MQSLEYPFT | 36C | MQSLEYPFT |

The humanized antibodies of the present invention, or antibody fragments thereof, may comprise SEQ ID NO: 43 or a sequence with at least 80%, preferably 85%, 90%, 95% and 98%, identity after optimal alignment with sequence SEQ ID No. 43 and/or SEQ ID NO: 44 or a sequence with at least 80%, preferably 85%, 90%, 95% and 98%, identity after optimal alignment with sequence SEQ ID No. 44.

The humanized antibodies or antibody fragments of the present invention may comprise variable regions encoded by polynucleotides having the nucleotide sequence of the murine light-chain variable region (SEQ ID NO: 45) or a sequence with at least 80%, preferably 85%, 90%, 95% and 98%, identity after optimal alignment with sequence SEQ ID No. 45 and/or the nucleotide sequence of the murine heavy-chain variable region (SEQ ID NO: 46) or a sequence with at least 80%, preferably 85%, 90%, 95% and 98%, identity after optimal alignment with sequence SEQ ID No. 46.

SEQ ID NO: 45 corresponds to the nucleotide sequence of the humanized heavy chain variable region of an antibody according to the present invention (Hz D-A10 Mab with descriptions of FR1, CDR1, FR2, CDR2, FR3 and CDR3 according to IMGT® presented in FIG. 18).

SEQ ID NO: 46 corresponds to the nucleotide sequence of the humanized light chain variable region of an antibody according to the present invention (Hz D-A10 Mab with descriptions of FR1, CDR1, FR2, CDR2, FR3 and CDR3 according to IMGT® presented in FIG. 18).

Figure 19:
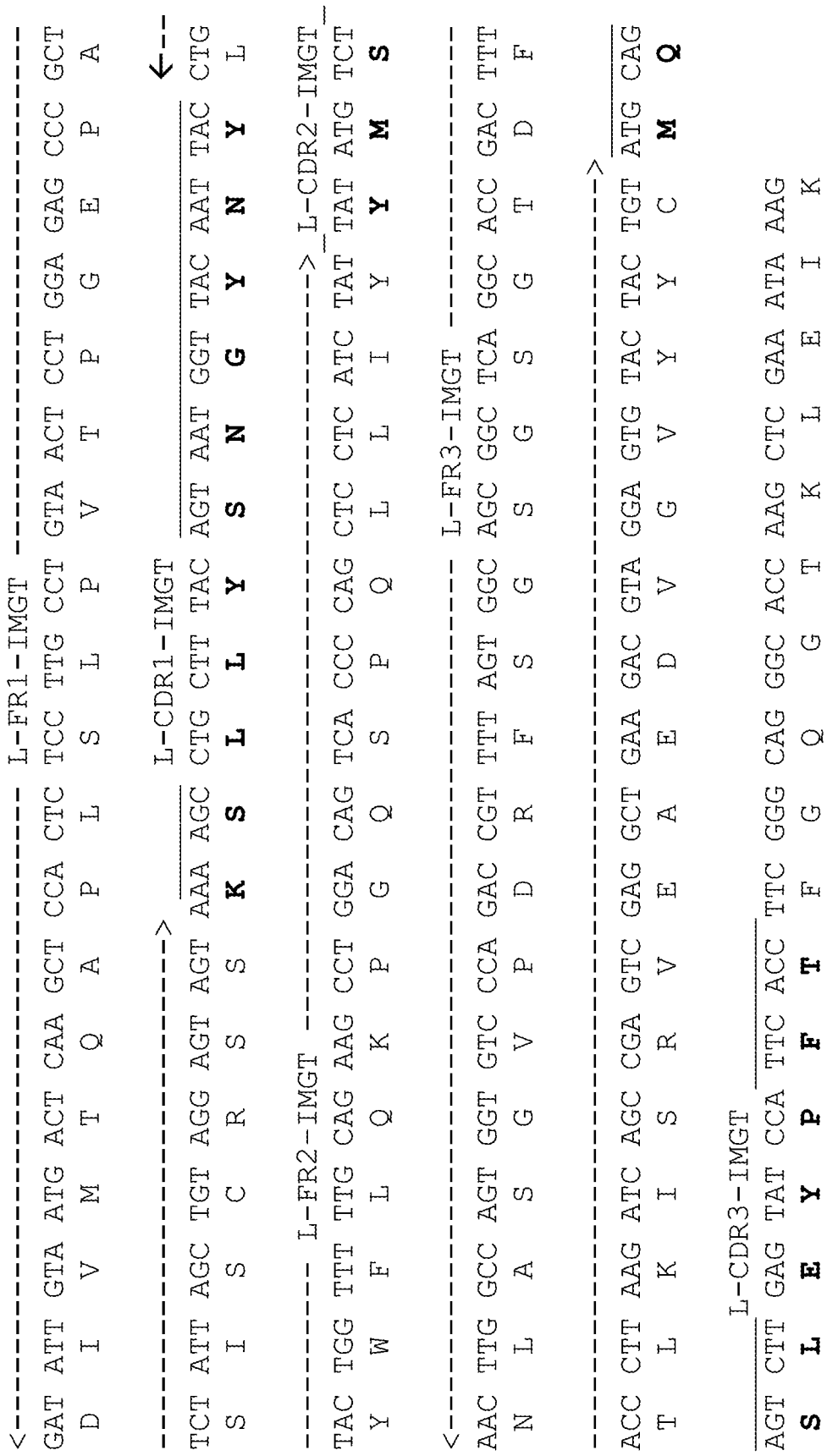
FIG. 19 illustrates the amino acid and nucleic acid sequences of the light chain variable (VL) region of the humanized monoclonal antibody derivate of the mD-A10 Mab.

SEQ ID NO: 43 corresponds to the amino acid sequence of the humanized light chain variable region of an antibody according to the present invention (Hz D-A10 Mab with descriptions of FR1, CDR1, FR2, CDR2, FR3 and CDR3 according to IMGT® presented in FIG. 19).

SEQ ID NO: 44 corresponds to the amino acid sequence of the humanized heavy chain variable region of an antibody according to the present invention (Hz D-A10 Mab with descriptions of FR1, CDR1, FR2, CDR2, FR3 and CDR3 according to IMGT® presented in FIG. 19).

The nucleic acid and amino acid sequences of the light-chain and heavy-chain variable regions of Hz D-A10 Mab are presented in Table 4.

TABLE 4

| Sequence codification for CDR VH or CDR VL of Hz D-A10 Mab | | |
|---|---|---|
| | VL nucleic acid sequence | VH nucleic acid sequence |
| Hz D-A10 | SEQ ID NO: 46 | SEQ ID NO: 45 |
| | VL amino acid sequence | VH amino acid sequence |
| Hz D-A10 | SEQ ID NO: 43 | SEQ ID NO: 44 |

The antibody fragment according to the present invention may be a F(ab')$_2$, Fab, Fv or ScFv fragment.

The antibodies or antibody fragments of the present invention efficiently inhibit the invasive capacity of tumor cells in vitro and effectively inhibit tumor growth in vivo. In particular, the Inventors have shown that the mD-A10 Mab effectively inhibits the invasive capacity of Isreco-1 cells in vitro (FIG. 4) and effectively inhibits the growth of Isreco 1 and HCT116 tumor cells in mice (FIGS. 7 to 10). In particular, the Inventors have shown that the mD-A10 Mab inhibits the invasive capacity of Isreco-1 cells in vitro whereas the antibody mD-D6 has no effect. This antagonistic activity is also observed with the antibody M20 (FIG. 4). In vivo, only the mD-A10 or M20 antibody also control tumor growth.

During apoptosis, cells undergo dramatic changes in morphology, partly due to a complete reorganization of their cytoplasmic and nuclear cytoskeletal structures. This breakdown process is well orchestrated and involves a stepwise activation of caspases. Some of the cytoskeletal components retain a function during different stages of apoptosis and are consequently only disassembled at later stages of the process. As during early apoptosis, procaspases-3 and -9 are specifically targeted to the CK8/18 intermediate filament network, this could explain the rapid breakdown of the cytokeratin scaffold during apoptosis.

Figure 6:
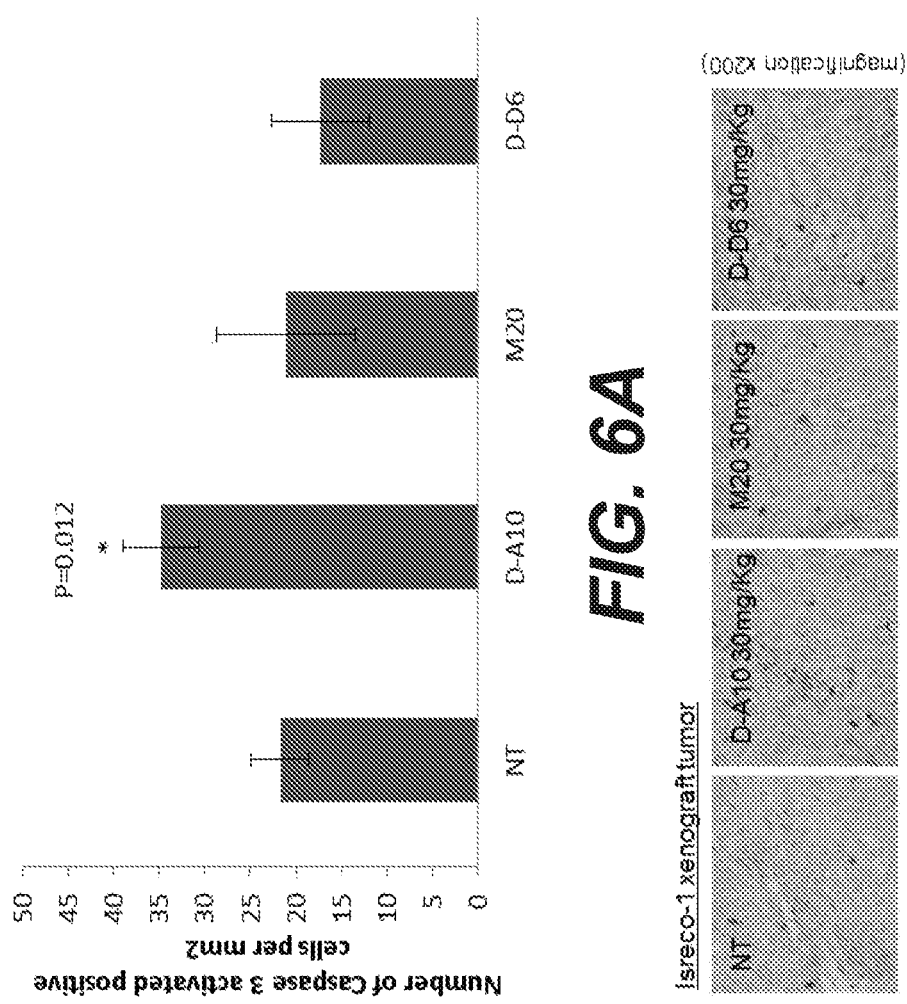
FIGS. 6A and B illustrate in vivo the effect of anti-CK8 antibodies on Caspase 3 activation from Isreco-1 tumor cells.

The inventors have shown that the mD-A10 or M20 antibody exhibit anti-tumoral growth effect by distinct molecular mechanism. Activation of Caspase 3 which indicates apoptosis efficiency was analyzed in tumors obtained in mice not treated (NT) and in mice treated by mD-A10, M20 or with mD-D6. The tumors analyzed in this experiment were those obtained and analyzed in the experiment corresponding to FIG. 7. At the end of the treatment (53 days), tumors were collected, fixed in buffered formalin and embedded in paraffin. Tissue sections were submitted to immunohistochemistry analyses with rabbit monoclonal anti cleaved caspase 3 antibody (FIG. 6B). For each tumor, the number of caspase 3 activated positive cells was counted on a surface of 2 mm². As shown in FIG. 6A the number of caspase 3 activated positive cells is significantly higher in tumors from animals treated with mD-A10 Mab compare to untreated animals and to animal treated with M20 or mD-D6.

This result clearly shows that mD-A10 Mab is able to induce caspase 3 cleavage related to Isreco-1 apoptosis in vivo whereas M20 and mD-D6 did not exhibit this ability. These results demonstrate that M20 and mD-A10 Mab exhibit their anti-tumoral growth effect by a very distinct mechanism. The mode of action of mD-A10 Mab relies on caspase 3 cleavage apoptosis induction. No similar effect was observed in the presence of the M20.

Thus, in some aspects, the present invention relates to an antibody or antibody fragment exhibiting specific agonistic activity on caspase 3 dependent cell apoptosis and exhibiting specific antagonistic activity on cell invasion. Therefore, it may be used for the treatment of diseases wherein CK8 is involved.

Figure 12:
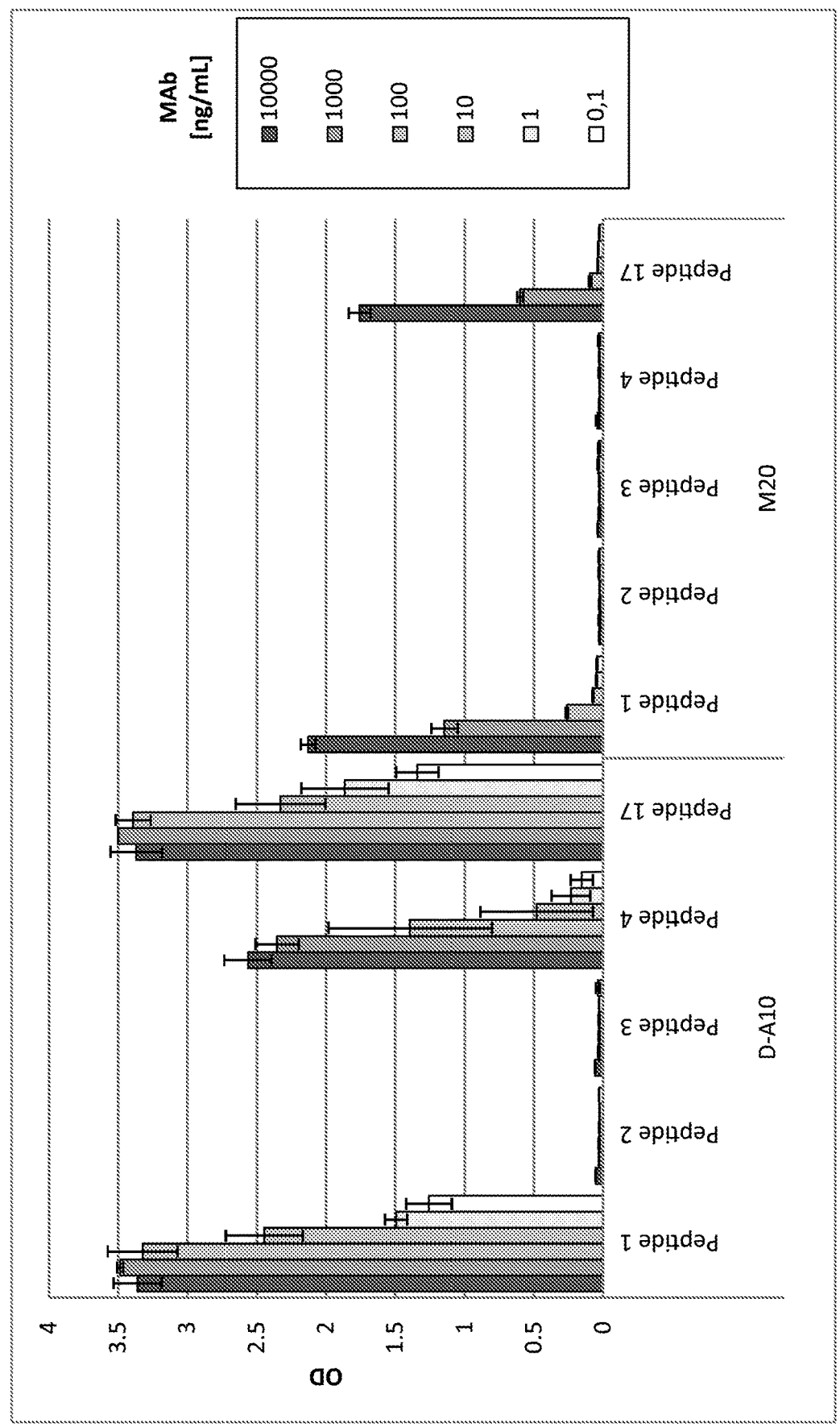
FIG. 12 illustrates the reactivity of the M20 antibody or the mD-A10 Mab for the BSA conjugated peptide 1 (SEQ ID NO: 1), 2 (SEQ ID NO: 2), 3 (SEQ ID NO: 3), 4 (SEQ ID NO: 4) or 17 (SEQ ID NO: 17), by ELISA.

While both mD-A10 Mab and M20 recognize human CK8 protein and have antagonistic properties, it has been shown that mD-A10 Mab and M20 do not recognize the same epitope (FIG. 2, FIG. 3, FIG. 12). Indeed, M20 specifically recognizes the peptides having the sequence corresponding to the amino acids from position 338 to 366 of human CK8 (SEQ ID NO: 1) or from position 345 to 366 of human CK8 (SEQ ID NO: 17) but does not detect peptides having the sequence corresponding to the amino acids from position 338 to 357 of human CK8 protein (SEQ ID NO: 2) or the sequence corresponding to the amino acids from position 358 to 366 of human CK8 protein (SEQ ID NO: 3) or the sequence corresponding to the amino acids from position 354 to 366 of human CK8 protein (SEQ ID NO: 4), whereas the mD-A10 recognizes both the peptide having the sequence corresponding to the amino acids from position 338 to 366 of human CK8 (SEQ ID NO: 1), the peptide having the sequence corresponding to the amino acids from position 354 to 366 of human CK8 (SEQ ID NO: 4) or the peptide having the sequence corresponding to the amino acids from position 345 to 366 of human CK8 (SEQ ID NO: 17) and does not detect peptides having either the sequence corresponding to the amino acids from position 338 to 357 of human CK8 (SEQ ID NO: 2) or the sequence corresponding to the amino acids from position 358 to 366 of human CK8 (SEQ ID NO: 3) (FIG. 12).

Moreover, detection using either flow cytometry (FIG. 2) or western blot (FIG. 3) of human CK8 protein isoforms by antibody M20 is inhibited neither by the peptide having the sequence corresponding to the amino acids from position 338 to 366 of human CK8 (SEQ ID NO: 1) nor by the peptide having the sequence corresponding to the amino acids from position 338 to 357 of human CK8 (SEQ ID NO: 2), whereas detection of human CK8 isoforms by mD-A10 Mab is strongly inhibited by the peptide having the sequence according to SEQ ID NO: 1 but not by the peptide having the sequence according to SEQ ID NO: 2 and detection of MAb D-D6 is inhibited by both peptides having the sequence according to SEQ ID NO: 1 and SEQ ID NO: 2.

The positioning of peptides 1 (SEQ ID NO: 1), 2 (SEQ ID NO: 2), 3 (SEQ ID NO: 3) and 4 (SEQ ID NO: 4) in the human cytokeratin-8 sequence (ref.: Uni-ProtKB P05787) is presented in FIG. 11.

Figure 13A:
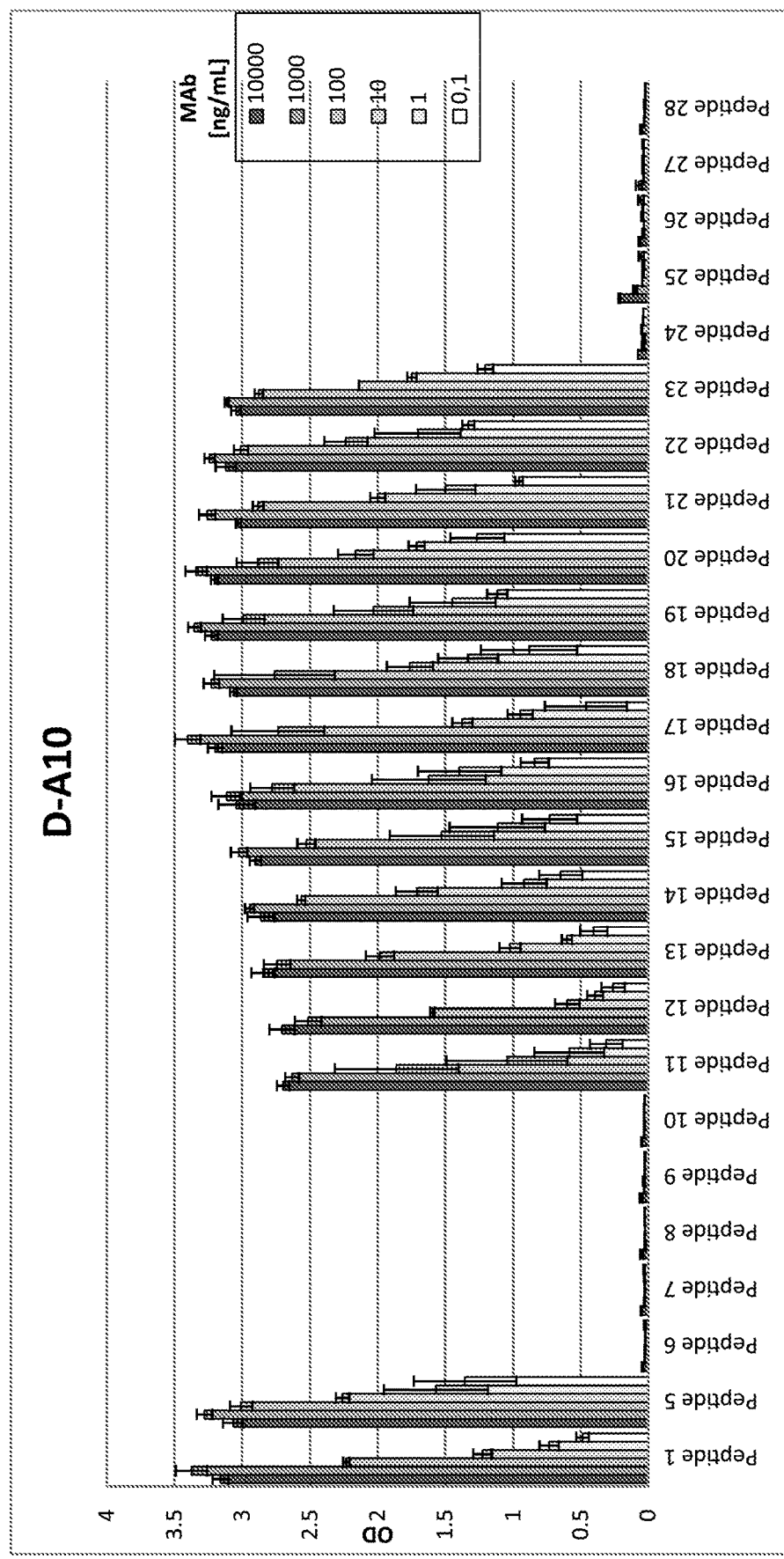
FIG. 13A illustrates the reactivity of the mD-A10 Mab for unconjugated coated peptides 1, 5 to 28 (SEQ ID NO: 1, SEQ ID NO: 5 to SEQ ID NO: 28) by ELISA.
Figure 13B:
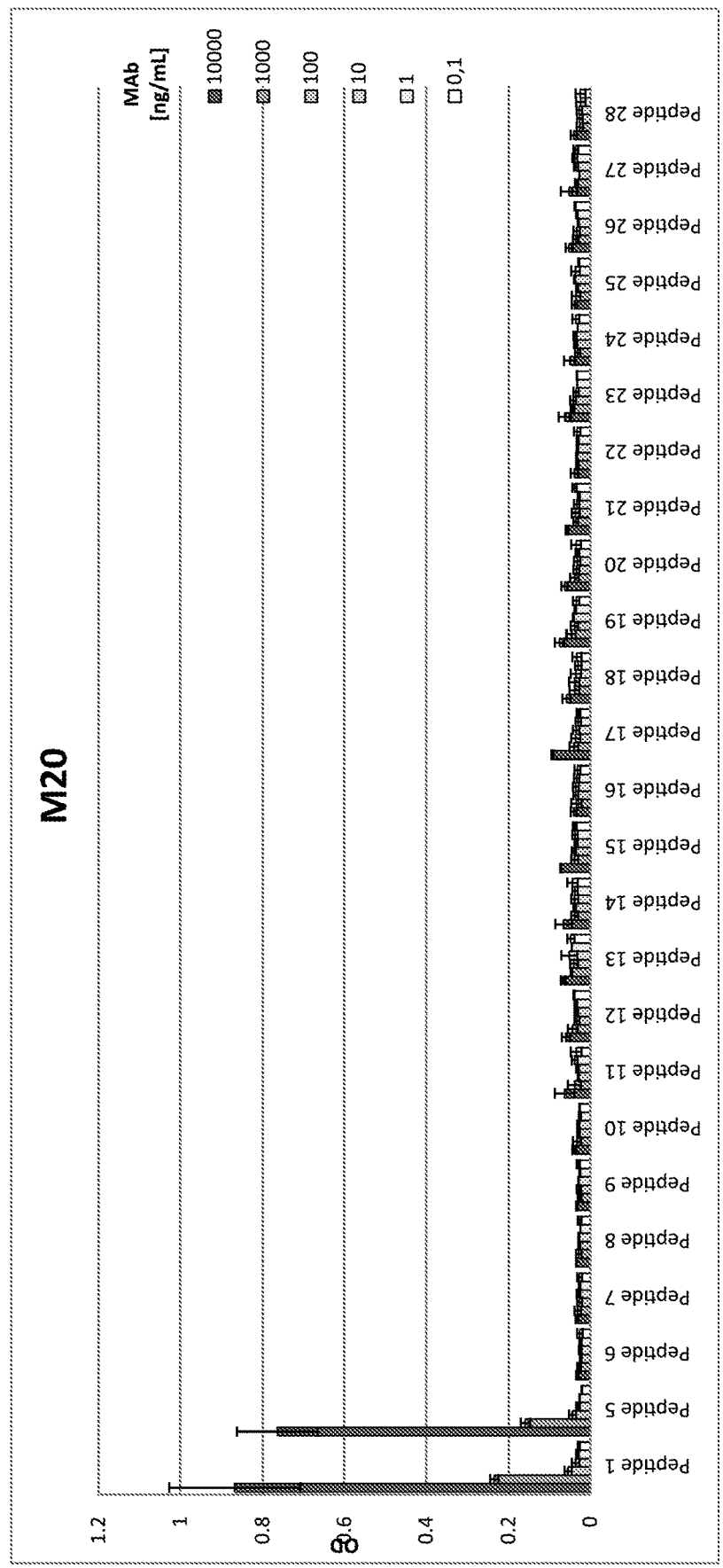
FIG. 13B illustrates the reactivity of M20 for unconjugated coated peptides 1, 5 to 28 (SEQ ID NO:1, SEQ ID NO: 5 to SEQ ID NO: 28) by ELISA.

FIG. 13A describes the reactivity of the mD-A10 Mab for anti-CK8 peptides delimited at the N- and C-terminus (peptide 1, peptide 5 to 28, SEQ ID NO:1, SEQ ID NO: 5 to SEQ ID NO: 28). The mD-A10 Mab binds to peptides 1, 5, 11 to 23. The leucine at position 353 of peptide 11 is essential for recognition by the antibody. Indeed, the binding of the mD-A10 Mab to peptide 10 is almost abolished compare to that of peptide 11. The leucine at position 360 of peptide 23 is essential for recognition by the antibody. Indeed, the binding of the mD-A10 Mab to peptide 24 is almost abolished compare to that of peptide 23. The essential presence of leucines at positions 353 and 360 of the epitope's sequence is confirmed by almost the non-competition of peptides 10 (SEQ ID NO: 10) and 24 (SEQ ID NO: 24) for recognition by the mD-A10 Mab using the ELISA technique (FIG. 14 and FIG. 15) when said competition is carried out with BSA conjugated peptide 1 or peptide 17, respectively. The epitope recognized by the mD-A10 Mab is thus designed as the 8-amino acid sequence "LSELEAAL" corresponding to the amino acids from position 353 to position 360 (SEQ ID NO: 29). As shown in FIG. 13B, a different M20 profile was observed compared to the mD-A10 Mab. By contrast, clearly, the antibody M20 does not recognize the epitope "LSELEAAL"

The set of amino acid sequences and the recognition or low or absence of recognition by the mD-A10 Mab of peptides 5 to 28 (SEQ ID NO: 5 to SEQ ID NO: 28) are presented in Table 8.

The present invention also relates to an antibody or to antibody fragments specifically binding to the peptide having the sequence corresponding to the amino acids from position 353 to position 360 of human CK8 protein, that is, specifically binding to the peptide having the sequence as shown in SEQ ID NO: 29, for use in the treatment of tumors whose cells express CK8 protein on their surface, in particular whose cells express the peptide of the sequence according to SEQ ID NO: 29 on their surface. The antibody or antibody fragments may be as described above.

Particularly, the antibody or antibody fragments of the present invention can be used to treat colorectal cancers, ovarian cancers, breast cancers, lung cancers, testicular cancers, pancreatic cancers, nervous system cancers, lymph node cancers, kidney cancers and/or head and neck cancers. Colorectal cancers, ovarian cancers, breast cancers, lung cancers, testicular cancers, pancreatic cancers, nervous system cancers, lymph node cancers, kidney cancers and/or head and neck cancers are characterized by the presence of tumor cells expressing CK8 protein on their surface. In particular, the antibodies or antibody fragments of the present invention can be used to treat invasive and/or metastatic colorectal cancers, ovarian cancers, breast cancers, lung cancers, testicular cancers, pancreatic cancers, nervous system cancers, lymph node cancers, kidney cancers and/or head and neck cancers.

Preferably, the antibodies or antibody fragments used therapeutically are humanized antibodies.

Peptides and Uses Thereof

The invention also relates to a human CK8 antigen peptide consisting of a polypeptide having from 8 to 16 amino acids and comprising the sequence of SEQ ID No. 29. In particular, the invention relates to a human CK8 antigen peptide consisting of the sequence according to SEQ ID NO: 29.

Such a peptide can be used as a therapeutic agent, in particular in a vaccine.

The invention also relates to a kit comprising a container containing a molecule specifically binding to said peptide. The kit can in particular be used for detecting cancer, in particular cancer characterized by the presence of tumor cells expressing CK8 protein on their surface, such as those described above.

Polynucleotides

The invention also relates to polynucleotides encoding the peptide derived from human CK8 having the sequence corresponding to the amino acids from position 353 to position 360 of human CK8 protein (SEQ ID NO: 29). Preferably, the polynucleotides of the invention are of DNA type, in particular of double-stranded DNA type. The term "polynucleotide" also refers to modified polynucleotides.

The polynucleotides of the present invention are isolated or purified from their natural environment. Preferably, the polynucleotides of the present invention can be produced by the conventional molecular biology techniques described by Sambrook et al. (Molecular Cloning: A Laboratory Manual, 1989) or by chemical synthesis.

The invention also relates to polynucleotides encoding the variable regions of the mD-A10 Mab having the nucleotide sequence of the murine light-chain variable region (SEQ ID NO: 30) and the nucleotide sequence of the murine heavy-chain variable region (SEQ ID NO: 32). Thus, the present invention also relates to polynucleotides that include one of the following sequences: SEQ ID NO: 30, SEQ ID NO: 32 or sequences with at least 80%, preferably 85%, 90%, 95% and 98%, identity after optimal alignment with sequence SEQ ID No. 30 or SEQ ID No. 32.

The invention also relates to polynucleotides encoding the variable regions of Hz DA-10 Mab having the nucleotide sequence of the humanized light-chain variable region (SEQ ID NO: 46) and the nucleotide sequence of the humanized heavy-chain variable region (SEQ ID NO: 45). Thus, the present invention also relates to polynucleotides that include one of the following sequences: SEQ ID NO: 45, SEQ ID NO: 46 or sequences with at least 80%, preferably 85%, 90%, 95% and 98%, identity after optimal alignment with sequence SEQ ID No. 45 or SEQ ID No. 46.

Pharmaceutical Compositions

The invention also relates to a pharmaceutical composition or a kit comprising an antibody or antibody fragments of the present invention. The antibody of antibody fragments may be as described above. In particular, the antibody or antibody fragment is Fv, Fab, F(ab')2, scFv, antibody, preferably a monoclonal antibody.

The pharmaceutical compositions may comprise an antibody or antibody fragment and a suitable pharmaceutical carrier. Examples of a suitable pharmaceutical carrier include solvents, gelatin, starch, lactose, magnesium stearate, talc, gum arabic or analogues. The compositions may further comprise dispersants, wetting agents, suspending agents, solubilizers, stabilizers, preservatives, flavor enhancers and/or sweeteners.

The kit may comprise a container containing an antibody or antibody fragments of the present invention.

The kit can in particular be used for detecting cancer, in particular cancer characterized by the presence of tumor cells expressing CK8 protein on their surface, such as those described above.

The compositions may be formulated for administration to mammals, in particular to humans. They may be formulated for oral, sublingual, subcutaneous, intramuscular, intravenous, transdermal, local or rectal administration. The compositions may thus be provided in all suitable forms depending on the desired modes of administration. They may thus be provided in the form of an oral or injectable solution or liquid suspension, or in solid or semi-solid form, in the form of powders, tablets, soft capsules, granules, sugar-coated tablets, hard capsules, sprays, cachets, pills, bars or pastes. The dosage varies according to the treatment and to the disorder concerned.

The compositions or kits may further comprise another antibody and/or another anti-cancer drug.

The invention also relates to the pharmaceutical composition of the invention for its use in the treatment or the prevention of a cancer, an autoimmune disease, an inflammatory condition, a viral infection or a viral disease and/or as a medicament to induce apoptosis of a tumour cell.

The invention also relates to a method for the treatment or the prevention of a cancer, an autoimmune disease, an inflammatory condition, a viral infection or a viral disease, and/or a method to induce apoptosis of a tumor cell comprising the administration to a mammal including human, of an effective amount of an antibody or antibody fragment according to the present invention.

The cancer are in particular characterized by the presence of tumor cells expressing CK8 protein on their surface, such as those described above.

The invention also relates to vaccine compositions comprising a peptide according to the present invention and a suitable adjuvant. In vaccines, adjuvants are typically defined as substances capable of potentiating or modulating the immune response against one or more co-administered antigens. Vaccines are usually injected, but they may be administered orally or via nasal spray.

The invention relates to pharmaceutical or vaccine compositions for the prevention and/or treatment of tumors whose cells express CK8 protein on their surface, in particular colorectal cancers, ovarian cancers, breast cancers, lung cancers, testicular cancers, pancreatic cancers, nervous system cancers, lymph node cancers, kidney cancers and/or head and neck cancers.

The invention also relates to methods for the therapeutic treatment and/or prevention of tumors whose cells express CK8 protein on their surface, in particular colorectal cancers, ovarian cancers, breast cancers, lung cancers, testicular cancers, pancreatic cancers, nervous system cancers, lymph node cancers, kidney cancers and/or head and neck cancers, comprising the administration to an individual in need thereof of an effective amount of an antibody or antibody fragment according to the present invention. The invention relates to methods of treatment of cancer via induction of CK8-expressing cancer cells death, in particular via induction of apoptosis in CK8-expressing cancer cells, by administration to an individual in need thereof of an effective amount of an antibody or antibody fragment according to the present invention. The antibody or antibody fragments may be as described above.

The invention relates to the use of antibodies or an antibody fragment according to the present invention for the manufacture of medicine for treating or preventing tumors whose cells express CK8 protein on their surface, in particular colorectal cancers, ovarian cancers, breast cancers, lung cancers, testicular cancers, pancreatic cancers, nervous system cancers, lymph node cancers, kidney cancers and/or head and neck cancers.

EXAMPLES

The M20 antibody referred to herein below is the commercially available antibody C5301 (Sigma) and the 1E8 antibody is the commercially available antibody ab28050 (abcam).

Preparation of Anti-CK8 Antibody

The murine monoclonal antibodies specific for CK8 were produced using standard hybridoma techniques (Zola et al., *Aust J. Exp Biol Med Sci.* 1981; 59:303-6). Two different CK8 related peptides were synthesized and used for mice immunization. The peptide sequences are as follows:

```
Peptide 1:
                                       (SEQ ID NO: 1)
AEQRGELAIKDANAKLSELEAALQRAKQD-C Peptide 2:
                                       (SEQ ID NO: 2)
AEQRGELAIKDANAKLSELE-C
```

The immunization was performed on three OF1 mice with a mixture of peptides 1 and 2 coupled to KLH. The spleens of mice whose serum was positive detected by CK8 related ELISA were selected. The splenocytes were fused with mouse myeloma line X63-Ag8.653. Hybridoma supernatants were screened for CK8 binding by ELISA and by Immunofluorescence cell staining on CK8 positive cell lines. After hybridoma cloning, two murine Mabs were obtained called mD-A10 and mD-D6. The D-A10 or D-D6 clone was injected into the peritoneum of nude mice. The ascitic fluid was purified by affinity chromatography on protein A column and then IgG were eluted at acid pH and then transferred to PBS. After concentration, the PBS solution containing IgG was filtered and the Mab concentration was determined at 280 nm Cell Lines The established human colon cancer (CC) Isreco-1, Isreco-2, Isreco-3, HCT116+/+, HCT116−/− or HT29 (CLB) were grown in Dulbecco's Modified Eagle's Medium (Sigma, St Quentin Fallavier, France) supplemented with 10% heat-inactivated fetal bovine serum (FBS) (Sigma, St Quentin Fallavier, France), 4 nM L-glutamine (Sigma, St Quentin Fallavier, France) and 50 U/mL, 50 µg/mL penicillin—streptomycine (Sigma, St Quentin Fallavier, France).

The established human breast adenocarcinoma cells MCF-7 (ATCC) were grown in Minimum Essential Medium Eagle (Sigma, St Quentin Fallavier, France) supplemented with 10% heat-inactivated foetal bovine serum (FBS), (Sigma, St Quentin Fallavier, France), 2 nM L-glutamine (Sigma, St Quentin Fallavier, France) and 100 U/mL, 100 µg/mL penicillin-streptomycine (Sigma, St Quentin Fallavier, France).

The established leukemia cells of human B-precursor cells Nalm-6 (DSMZ), of Burkitt's human lymphoma cells Raji (ECACC), of non-Hodgkin lymphoma human RL (DSMZ), of histiocytic lymphoma U937 (ECACC), the human acute lymphoblastic leukemia cells Cem (DSMZ), leukemia cells established human acute lymphoblastic Molt4 (DSMZ), human plasma cells Fravel (ECACC) were grown in RPMI-1640 Medium (Sigma, St Quentin Fallavier, France) supplemented with 10% heat-inactivated fetal bovine serum (FBS), (Sigma, St Quentin Fallavier, France), 4 nM L-glutamine (Sigma, St Quentin Fallavier, France) and 100 U/mL, 100 µg/mL penicillin—streptomycine (Sigma, St Quentin Fallavier, France).

Antibody Cell Labelling Analyzed by Flow Cytometry

The CK8 cellular expression at the cell surface was analysed by flow cytometry. Briefly, $2.10^5$ cells per 96-wells were incubated with a dilution of unconjugated anti-CK8 murine Mab at 10 µg/mL then diluted at 1/10. Unbound antibodies were washed away with PBS (Invitrogen, Villebon sur Yvette, France) supplemented by 1% Bovine Serum Albumin (Sigma, St Quentin Fallavier, France). Subsequently, cells were centrifuged (5 min at 400 g) and bound antibody was detected with Fluorescein Isothiocyanate (FITC) conjugated goat (Fab')$_2$ polyclonal anti mouse (MP Biomedical, Illkirch, France) at 4° C. for 30 min. Detection reagent was washed away and cells were centrifuged (5 min at 400 g) and suspended in 300 µL PBS. Bound detection antibody is quantified on a FACS CAN (BD Biosciences, Rungis, France), (FL1 channel, 2 000 events per acquisition).

Results of experiments are shown in Table 5 with MAb concentration at 5 µg/mL. Various cancer cell lines such as colon or breast cell lines expressed CK8. No expression was observed in cells of lymphoma or leukemia.

TABLE 5

MAb cellular reactivity on human cell lines

| Cell line | | 1E8 | | M20 | | D-D6 | | D-A10 | |
|---|---|---|---|---|---|---|---|---|---|
| Name | Cell line type | % | IFM | % | IFM | % | IFM | % | IFM |
| ISRECO-1 | Human colon carcinoma | 45 +/− 18 | 562 +/− 144 | 50 +/− 11 | 553 +/− 69 | 50 +/− 7 | 421 +/− 32 | 47 +/− 7 | 421 +/− 46 |
| ISRECO-2 | Human colon carcinoma | 23 +/− 0 | 424 +/− 28 | 26 +/− 0 | 473 +/− 30 | 44 +/− 26 | 317 +/− 80 | 43 +/− 27 | 323 +/− 89 |
| ISRECO-3 | Human colon carcinoma | 41 +/− 6 | 402 +/− 105 | 33 +/− 6 | 541 +/− 13 | 43 +/− 3 | 340 +/− 40 | 42 +/− 4 | 351 +/− 21 |
| HCT116 +/+ | Human colon carcinoma | 35 +/− 14 | 554 +/− 62 | 29 +/− 11 | 527 +/− 64 | 44 +/− 19 | 356 +/− 1 | 36 +/− 21 | 396 +/− 16 |
| HCT116−/− | Human colon carcinoma | 38 +/− 11 | 530 +/− 52 | 28 +/− 10 | 517 +/− 59 | 32 +/− 6 | 385 +/− 13 | 33 +/− 2 | 411 +/− 11 |
| HT29 | Human colon adenocarcinoma | 30 +/− 7 | 418 +/− 11 | 17 +/− 9 | 497 +/− 52 | 28 +/− 13 | 365 +/− 15 | 27 +/− 13 | 361 +/− 3 |
| MCF-7 | Breast adenocarcinoma | 52 +/− 1 | 462 +/− 1 | 66 +/− 17 | 476 +/− 10 | 51 +/− 23 | 388 +/− 13 | 50 +/− 23 | 397 +/− 30 |
| Nalm6 | Human B-cells precursor leukaemia | 0+/0 | — | 0 +/− 0 | — | 0+/0 | — | 0 +/− 0 | — |
| Raji | Human Burkitt's lymphoma | 0+/0 | — | 0 +/− 0 | — | 0+/0 | — | 0 +/− 0 | — |
| RL | Human non Hodgkin's lymphoman B-cell | 0+/0 | — | 0 +/− 0 | — | 0+/0 | — | 0 +/− 0 | — |
| U937 | Human hidtiocytic lymphoma | 0 +/− 0 | — | 0 +/− 0 | — | 0 +/− 0 | — | 0 +/− 0 | — |
| Cem | Human acute lymphoblastic leukaemia | 0 +/− 0 | — | 0 +/− 0 | — | 0 +/− 0 | — | 0 +/− 0 | — |
| Molt4 | Human acute lymphoblastic leukaemia | 0 +/− 0 | — | 0 +/− 0 | — | 0 +/− 0 | — | 0 +/− 0 | — |
| Fravel | Human plasma cells | 0+/0 | — | 0 +/− 0 | — | 0+/0 | — | 0 +/− 0 | — |
| PBMNC | Lymphocytes | 0 +/− 0 | — | 0 +/− 0 | — | 0 +/− 0 | — | 0 +/− 0 | — |

Flow Cytometry Experiments for mAb Competition Binding.

$2.10^5$ Isreco-1 cells per 96-wells were incubated with a biotinylated antibody anti-CK8 (12.5 μg/mL) with or without peptide 1 or peptide 2 tested at different concentrations and incubated at 4° C. for 30 min. Unbound antibody was washed away with PBS (Invitrogen, Villebon sur Yvette, France) supplemented by 1% Bovine Serum Albumin (Sigma, St Quentin Fallavier, France). Subsequently, cells were centrifuged (5 min at 400 g) and bound antibody was detected with Phycoerythrin conjugated Streptavidin (Interchim, Montlucon, France) at 4° C. for 30 min. Detection reagent was washed away and cells were centrifuged (5 min at 400 g) and suspended in 300 μL PBS. Bound detection antibody was quantified on a FACS CAN (BD Biosciences, Rungis, France), (FL2 channel, 2 000 events per acquisition). During the experiment, the respective isotype controls were included to exclude any unspecific binding events. Results of experiments are shown in FIG. 2. The presence of peptide 1 inhibits cell labelling with the mD-D6 or mD-A10 Mab without any significant impact on M20 Mab cellular staining.

Detection of the Isoforms of CK8 Protein by Western Blotting

The different isoforms, together with their estimated molecular masses (kDa) and their corresponding amino acid sequence are shown in Table 6.

TABLE 6

Description of the different CK8 isoforms

| Proteic forms of CK8 | MM estimated (kDa) | Sequence corresponding (AA) |
|---|---|---|
| E' (longer form Extension N term) | 57 | 1-511 |
| E (whole) | 54 | 1-483 |
| I (indetermined) | 51, 49, 48, 47, 46 | ? |
| C (C term cleaved) | 43 | Estimated 1-393 |

E: CK8 entire Form,
I: indefinite CK8 isoform,
C: CK8 truncated isoform of C terminal In western blotting experiments (WB), five micrograms of proteins from a lysate of Isreco-1 colorectal cancer cells were separated by SDS-PAGE and transferred onto a nitrocellulose membrane. The membrane was saturated with a solution of TBS-T (Tris-HCl 20 mM pH 7, NaCl 130 mM, Tween 20 at 0.1%) containing 5% milk, then incubated with various anti-CK8 antibodies diluted in TBS-T solution containing 2.5% milk. The M20 (50 μg/mL), 1E8 (1/500), mD-A10 (1 μg/mL) or mD-D6 (1 μg/mL) antibodies were incubated for 1 h at room temperature with the membrane. The primary antibodies were revealed with anti-mouse secondary antibody coupled to peroxidase (HRP), (ab97040), (Abcam, France). The results are shown in FIG. 1. Isoforms of CK8 protein are differently detected depending on the antibody anti-CK8 tested. The full-length form of CK8 protein (CK8-E) is detected by all the antibodies. The C-terminal truncated form of CK8 protein (CK8-C) is strongly detected only by the mD-A10 antibody and weakly detected by M20. The 1E8 or mD-D6 Mab do not recognize the CK8-C form. These results clearly demonstrate that mD-A10 Mab exhibits a specific reactivity profile against the different CK8 isoforms compared to the other antibody anti CK8 tested.

Western Blot Competition Assay with CK8 Peptides

For the competition experiments, the antibody M20 (1 μg/mL) or murine monoclonal antibodies such as mD-A10 (1 μg/mL) or mD-D6 (1 μg/mL) were pre-incubated for 2 hours at room temperature with peptide 1 or peptide 2 with a molecular ratio of 1/100 (one antibody molecule per 100 peptide molecules) in a TBS-T solution. The antibody-peptide mixture was then brought into contact with the membranes in a solution of TBS-T with 2.5% milk for 1 hour for a revelation by an anti-mouse secondary antibody coupled to HRP. The results are shown in FIG. 3. The presence of peptide 2 decrease the recognition of all CK8 isoforms by the mD-D6 Mab and does not interfere with the recognition of the CK8 isoforms by the antibody M20 and by the mD-A10 Mab. Conversely, the presence of peptide 1 strongly decrease recognition of all CK8 isoforms by the mD-A10 and mD-D6 Mabs whereas it does not interfere with the recognition of the CK8 isoforms by the antibody M20.

Effect of the Murin Monoclonal Antibody D-A10 on the Colorectal Cancer Isreco-1 Cells' Invasive Capacities: In Cellulo Analysis of the Cancer Cells Invasive Capacities by Real Time Measurement of Cells Impedance (xCELLigence-ACEA Biosciences™ System)

The real time measurement instrument xCELLigence (ACEA Biosciences™) is based on impedance value which is proportional to cell fixation on microelectrodes. The system used to evaluate the cells' invasion capacities is the RTCA DP system. This system uses CIM plates containing 16 wells. Wells are formed by a lower and an upper chamber. The upper chamber communicates with the lower chamber through 8 μM diameter pores which are above the microelectrodes. When evaluating Isreco-1 invasion capacities, the lower chamber contained culture medium supplemented with 10% fetal bovine serum (FBS). The Isreco-1 cells (20 000 cells) in presence of culture medium without FBS are placed in the upper chamber with or without the anti-CK8 antibody (M20, mD-A10 or mD-D6 at 50 μg/mL). This upper chamber was previously covered at its bottom by a layer of matrigel (Matrigel™, BD biosciences). During the invasion process, cells are attracted by the FBS gradient established between the lower and upper chamber, degrade the matrigel allowing them to migrate through the pores and contact the micro-electrodes of the lower chamber. The impedance measurement generated by cell contact is measured every 15 min during 70 hours and is recorded by a computer linked to the RTCA DP system. The results of the invasive capacities of the cells are presented on FIG. 4. The percentage of inhibition of the Isreco-1 invasive capacities is represented with the standard deviation corresponding to 3 independent experiments. A significant inhibition on FBS triggered invasive capacities of Isreco-1 cells was observed in the presence of the antibody M20 or mD-A10, without any impact with the mD-D6.

Cell Viability Analysis Following ATP Level Determination

Figure 5:
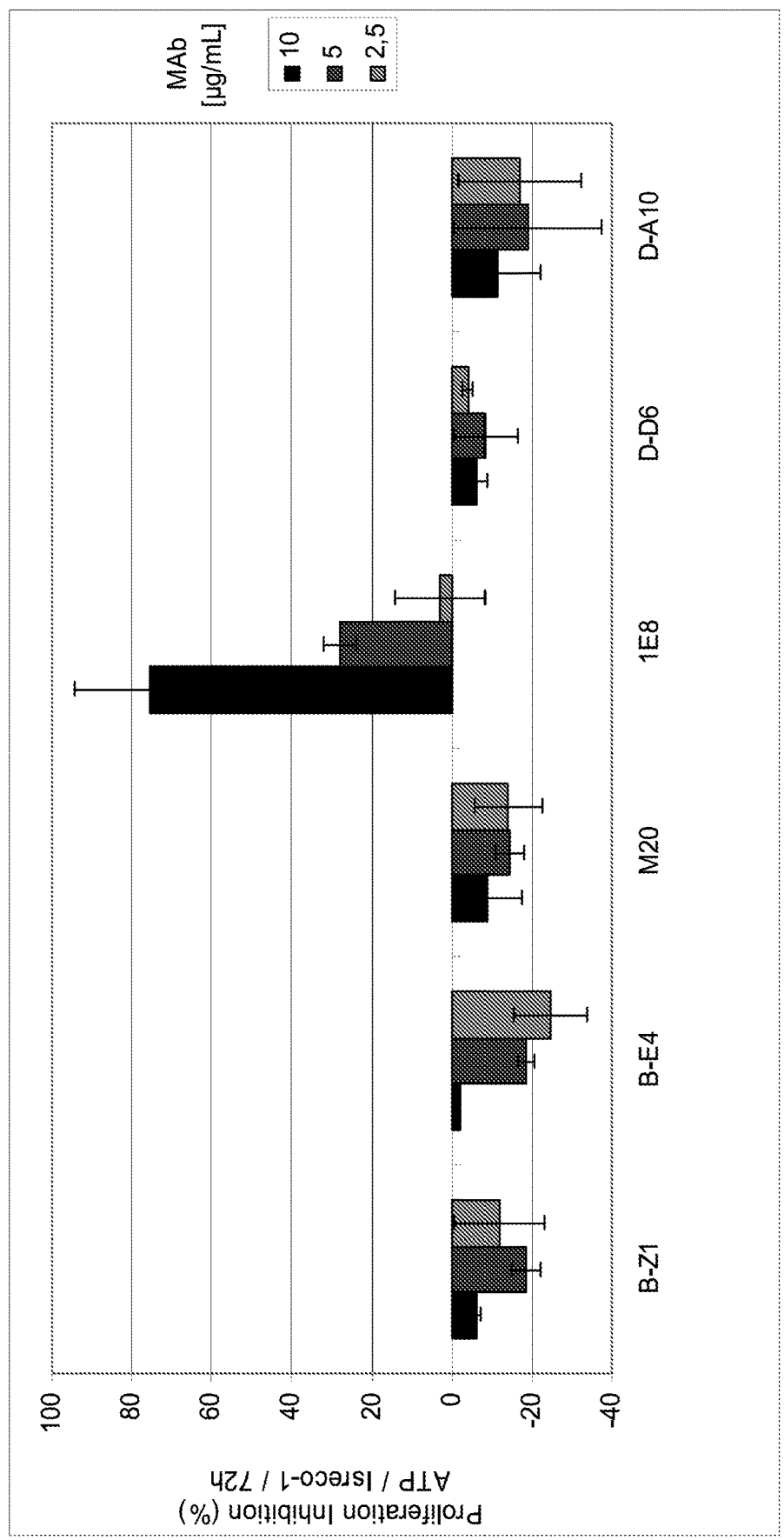
FIG. 5 illustrates the effect of anti-CK8 antibodies on Isreco-1 cell proliferation.

The CellTiter-Glo® Luminescent Cell Viability Assay (Promega, Charbonnieres les Bains, France) was used to determine the number of viable cells in culture based on quantification of the ATP present, an indicator of metabolically active cells. Detection is based on using the luciferase reaction to measure the amount of ATP from viable cells. Within minutes after a loss of membrane integrity, cells lose the ability to synthesize ATP, and endogenous ATPases destroy any remaining ATP; thus the levels of ATP fall precipitously. Cell cultures ($5.10^4$ cells/mL) were incubated for 72 hours alone or in the presence of the antibodies (B-Z1, B-E4, M20, 1E8, D-D6, D-A10) tested at 10 μg/ml and then diluted at 1/10 (FIG. 5). The isotype control Mabs (IgG1-B-Z1, IgG2a-B-E4) were purchased by Diaclone (Besangon, France). The CellTiter-Glo® reagent was added directly to cells in culture at a ratio of 50 μL of reagent to 200 μL of culture medium. The assay plates were incubated at room temperature for 10 min and the bioluminescent signal was recorded using a standard multiwell fluorometer Mithras LB940, (Berthold, Thoiry, France). The results are shown in FIG. 5. Only the Mab 1E8 anti-CK8 inhibits Isreco-1 cell proliferation.

Quantification of Caspase 3 Activated Positive Cells Accumulation in Isreco-1 Xenograft Tumor by Immunohistochemistry Staining Tissues were isolated from Isreco-1 xenograft tumors of mice treated or not by Mab at 30 mg/kg. The potency of antibody M20, mD-A10 or mD-D6 to induce caspase 3 activation was evaluated. For staining, tissue samples were fixed in 10% buffered formalin and embedded in paraffin. 4-μm-thick tissue sections of formalin-fixed, paraffin-embedded tissue were prepared according to conventional procedures. Immunohistochemistry was performed on an automated immunostainer (Ventana Discovery XT, Roche, Meylan, France) using DABmap Kit according to the manufacturer's instructions. After retrieval procedures with buffer Cell Conditioning 1 (CC1), sections were incubated with Rabbit monoclonal anti cleaved caspase 3 antibody (diluted 1:200, clone 5A1E, Cell signaling). Staining was visualized with DAB solution with 3,3'-diaminobenzidine as a chromogenic substrate. Finally, the sections were counterstained with Gill's hematoxylin. Quantification of number of caspase 3 activated positive cells per $mm^2$ were done by Histolab software coupled to camera after microscope visualization. For each tumor, counting of number of caspase 3 activated positive cells were realized on a surface of 2 $mm^2$. Necrotic area of the tumor and fibrous capsule were excluded from the analysis. The results of the quantification of the activated caspase 3 are presented on FIG. 6A. The number of caspase 3 activated positive cells is represented with a standard deviation corresponding to three mice per group. In FIG. 6B, an example of immunohistochemistry analysis is shown for thick tissue sections obtained from untreated animals and from animals treated with mD-A10 Mab, M20 and mD-D6 Mabs. As shown in FIG. 6A, the number of caspase 3 activated positive cells is significantly higher in tumors from animals treated with mD-A10 Mab compare to the untreated animals. No significant impact was observed in animals treated with M20 or with mD-D6 Mabs. This result clearly shows that mD-A10 Mab is able to induce the apoptosis related to the caspase 3 activation of Isreco-1 cells in vivo whereas M20 or mD-D6 Mab did not trigger the caspase cleavage. These results demonstrate that M20 and mD-A10 exhibit their anti-tumoral growth effect by a very distinct mechanism. The mD-A10 Mab is defined as an agonistic Mab related on caspase 3 triggered apoptosis induction while the M20 Mab is independent of this pathways.

Figure 7:
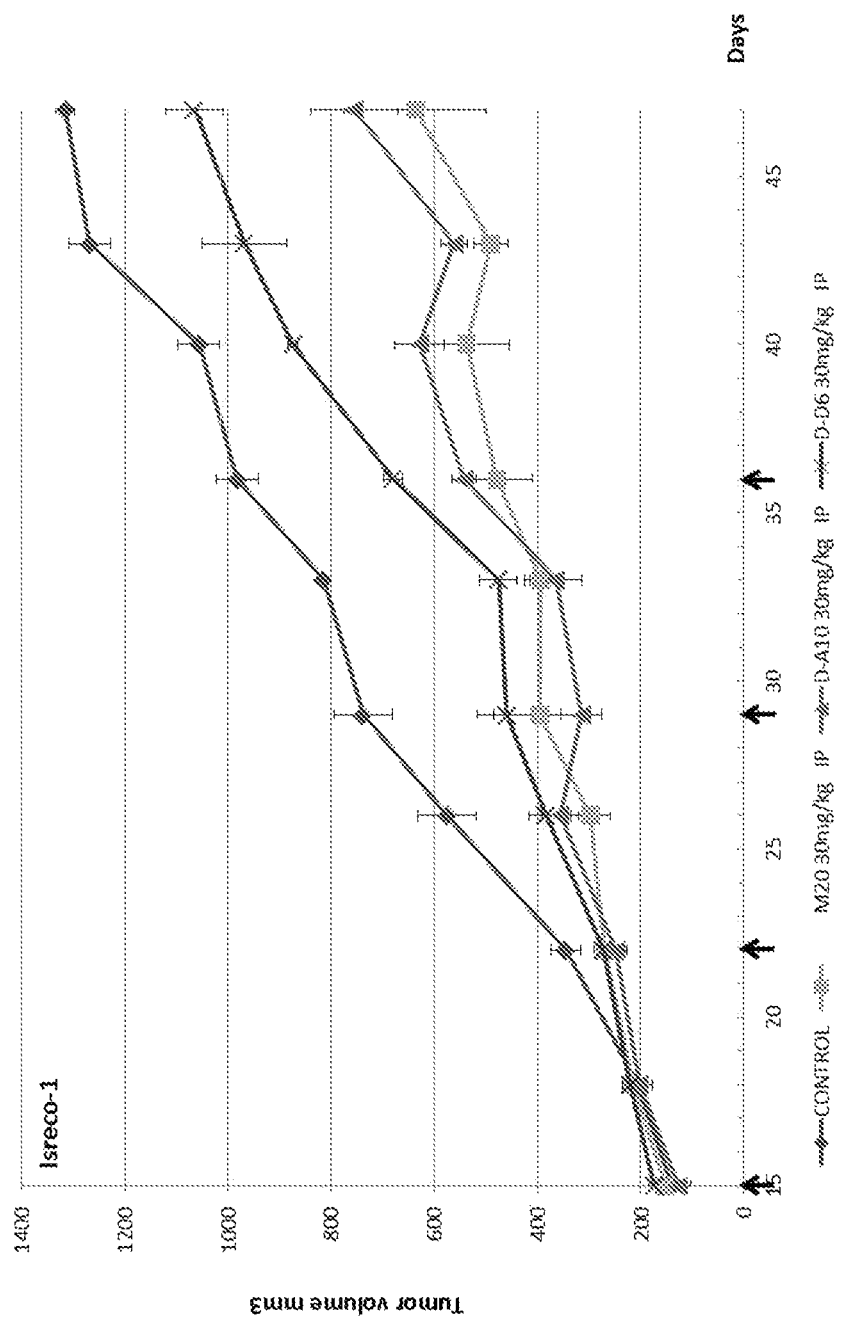
FIG. 7 illustrates the effect of anti-CK8 antibodies including the mD-A10 Mab on tumor (Isreco-1) growth in mice.
Figure 8:
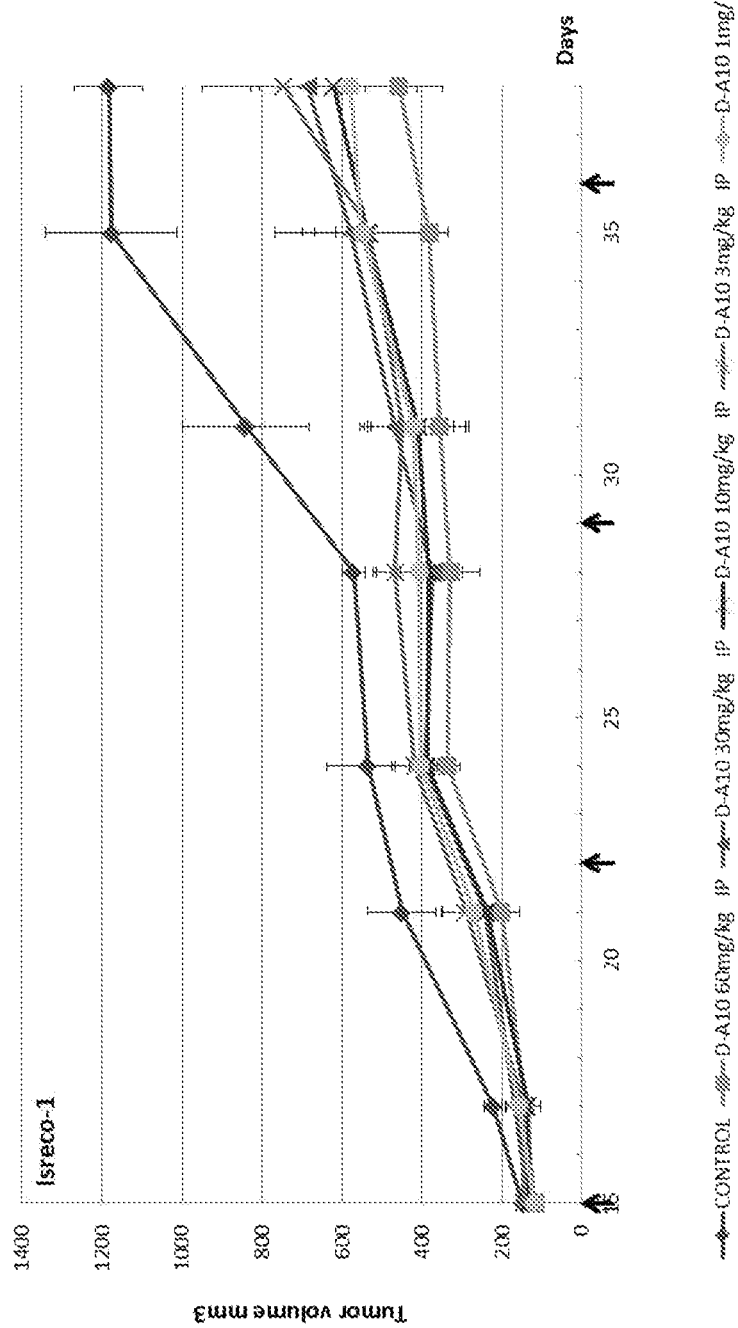
FIG. 8 illustrates the dose-dependent effect of the concentration of the mD-A10 Mab on tumor (Isreco-1) growth in mice.
Figure 9:
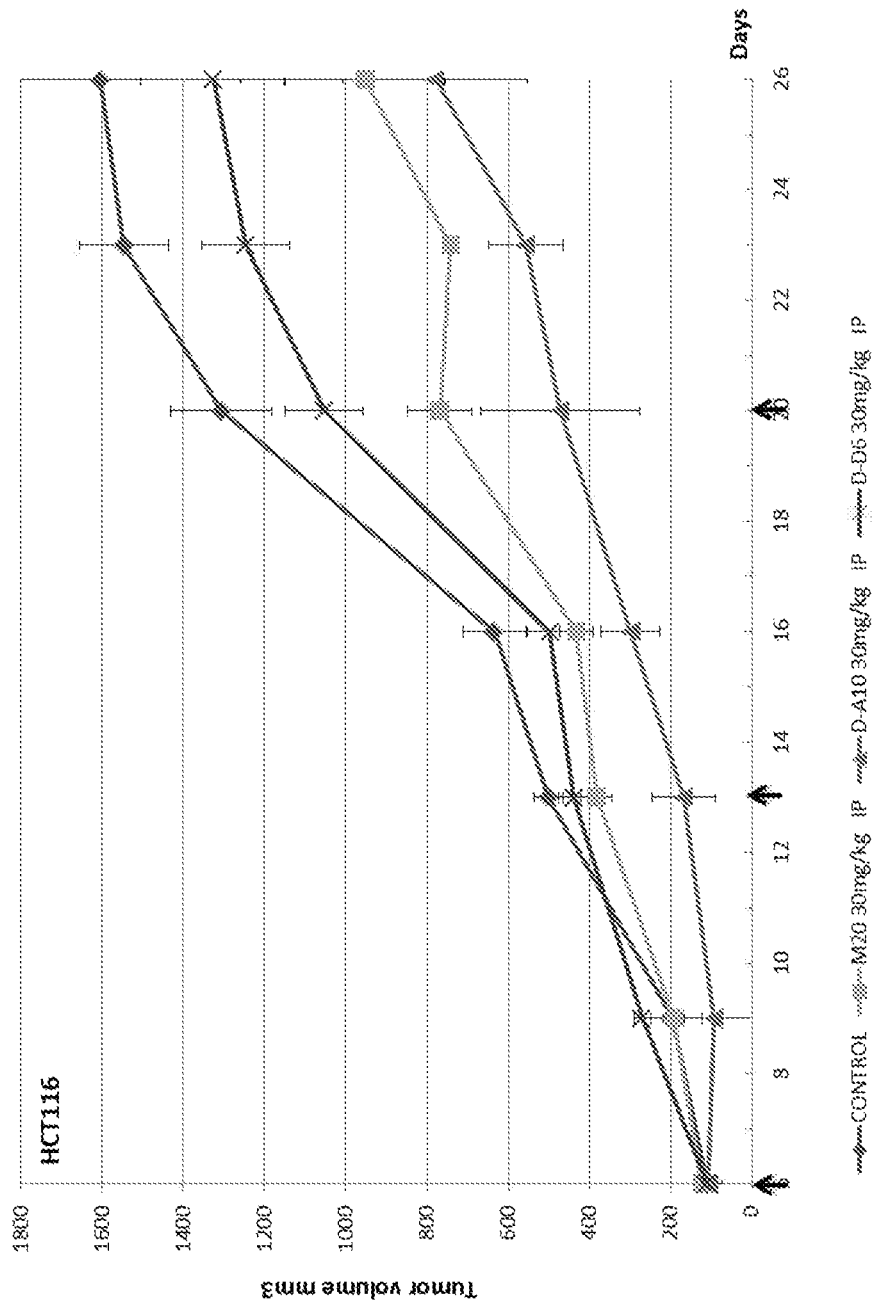
FIG. 9 illustrates the effect of anti-CK8 antibodies including the mD-A10 Mab on tumor (HCT116) growth in mice.

Effect of the Antibody Anti-CK8 on Tumoral Growth of Isreco-1 Colorectal Cancer Cells Subcutaneously Implanted in Mice Isreco-1 cells ($10 \times 10^6$) were injected subcutaneously in 12 SCID CB17 mice. After 15 days, the tumor reached a volume between 100 and 150 $mm^3$. At this time, mice were divided into 4 groups of three mice. Each group received or not a specific treatment by intraperitoneal injection performed at the opposite site of the tumor. Once a week during 4 weeks (days 15, 22, 29 and 36), mice received or not an injection of 30 mg/kg with the antibody M20, mD-A10 Mab or mD-D6 (FIG. 7). For each mouse, the tumor volume was measured twice weekly throughout the experiment. The average of the tumor volume of each mice group is represented on the graph with a standard deviation corresponding to three mice per group. As shown in FIG. 7, the antibody M20 or mD-A10 inhibited the growth of Isreco-1 colorectal cancer cells subcutaneously implanted in mice, whereas the mD-D6 did not control the tumor development.

Dose-Dependent Effect of the mD-A10 Mab on Tumoral Growth of Isreco-1 Colorectal Cancer Cells Subcutaneously Implanted in Mice Tumor Isreco-1 fragments obtained from colorectal cancer cells Isreco-1 were implanted subcutaneously in 18 SCID CB17 mice. After 15 days tumors reached a volume between 100 and 150 $mm^3$. At this time mice were divided into six groups of three mice. Each group received or not a specific treatment by intraperitoneal injection performed at the opposite site of the tumor. Once a week during 4 weeks (days 15, 22, 29 and 36), mice received or not an injection of 1 mg/kg 3 mg/kg, 10 mg/kg, 30 mg/kg or 60 mg/kg of mD-A10 Mab. For each mouse, the tumor volume was measured twice weekly throughout the experiment. The average tumor volume of each mice group is represented on the graph with a standard deviation corresponding to three mice per group. Results are presented in FIG. 8. The inhibition of the growth of Isreco-1 colorectal cancer cells subcutaneously implanted in mice was observed even at the lowest Mab concentration at 1 mg/kg.

Effect of mD-A10 Mab on Tumoral Growth of HCT116 Colorectal Cancer Cells Subcutaneously Implanted in Mice The HCT116 cells (10×10$^6$) were injected subcutaneously in 12 SCID CB17 mice. After 6 days, the tumor reached a volume between 100 and 150 mm$^3$. At this time, mice were divided in four groups of three mice. Each group received or not a specific treatment by intraperitoneal injection performed at the opposite site of the tumor. Once a week during 3 weeks (days 6, 13, and 20), mice received or not an injection of 30 mg/kg of the antibody anti-CK8 (M20, mD-A10 or mD-D6. For each mouse, the tumor volume was measured twice weekly throughout the experiment. The average volume of each group of mice is shown in the graph with a standard deviation equal to 3 mice per group. As shown in FIG. 7, the mD-A10 inhibited at the highest level the growth of Isreco-1 colorectal cancer cells subcutaneously implanted in mice compared to the antibody M20, whereas the mD-D6 did not control the tumor development.

Dose-Dependent Effect of the Concentration of mD-A10 Mab on Tumor Growth of HCT116 Colorectal Cancer Cells Implanted Subcutaneously in Mice.

Figure 10:
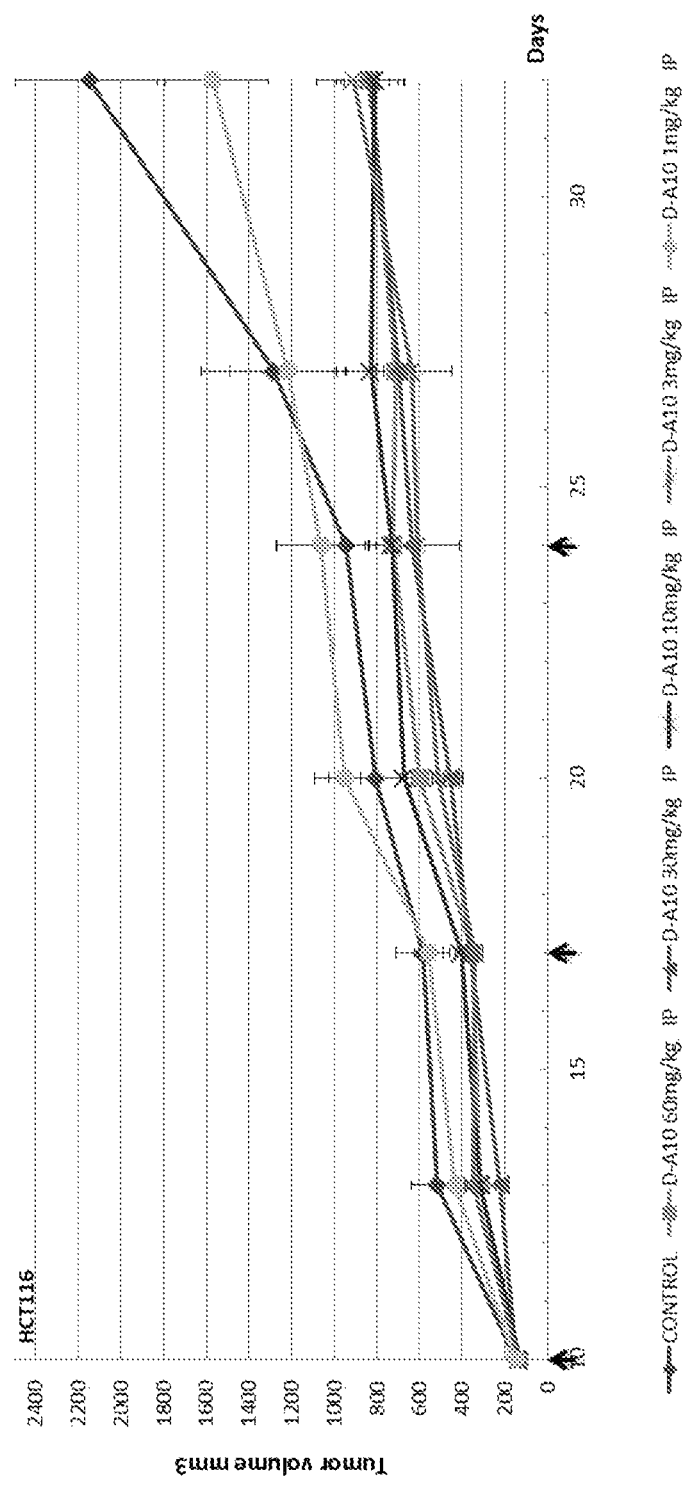
FIG. 10 illustrates the dose-dependent effect of the concentration of the mD-A10 Mab on tumor (HCT116) growth in mice.

The HCT116 cells (10×10$^6$) were injected subcutaneously in 18 SCID CB17 mice. After 10 days the tumor reached a volume between 100 and 150 mm$^3$. At this time, the mice were divided into six groups of three mice. Each group received or not a specific treatment by intraperitoneal injection at the opposite site of the tumor. Once a week for three weeks (days 10, 17, and 24), the mice were treated or not with 1 mg/kg, 3 mg/kg, 10 mg/kg, 30 mg/kg or 60 mg/kg of mD-A10 Mab. For each mouse, the tumor volume was measured twice weekly throughout the experiment. The average volume of each group of mice is shown in the graph with a standard deviation equal to three mice per group. The results are shown in FIG. 10.

Preparation of the Humanized Mab Anti-CK8 Derivate from the mD-A10 Mab

The DNA encoding the antibody is isolated and sequenced using conventional procedures (e.g. by using oligonucleotide probes that are capable of binding specifically to genes encoding the heavy and light chains of murine antibodies). The hybridoma cells serve as a preferred source of such DNA.

Conversion of Murine Mab to Native Chimeric Mab

The cDNA corresponding to the variable region from the hybridoma was obtained using two approaches. The first approach consisted to the utilisation in PCR of the degenerate N-term amino acid related primer set generate since the N-Terminal sequencing. The second approach consisted to the utilisation in PCR of degenerate primer set generate by IMGT® primer database and specific primers previously described (Essono et al., *J Immunol Methods*. 2003; 203: 279:25-66, Wang et al., *Mol Immunol*. 1991; 28:1387-97). The sequence of N-terminal variable region was determined by Edman degradation. Total RNA extraction was carried out using the Tri Reagent kit according to the protocol described by the supplier Sigma. The amplified VL and VH fragments were cloned into the TOPO-TA cloning vector (Invitrogen) for sequence analyses by the di-deoxy-termination method (Sanger et al., *Nature*. 1977; 265:687-95). Then antibody variants constructs were amplified by PCR and cloned into the expression vector.

Positions are numbered according to IMGT®, to Kabat® index and to Common Numbering Systems (Identical V region amino acid sequences and segments of sequences in antibodies of different specificities). Relative contributions of VH and VL genes, mini-genes, and complementarity-determining regions to binding of antibody-combining sites were analysed (Kabat et al., *NIH Publ*. 1991; No. 91-3242, Vol. 1, 647-669).

The nucleic acid sequence or amino acid sequence regarding the chimeric D-A10 Mab are shown in the Sequence Listing:

nucleotide sequence of the variable murine light chain of mD-A10 Mab (SEQ ID NO:30) and its derived amino acid sequence (SEQ ID NO:31).

nucleotide sequence of the variable murine heavy chain of mD-A10 Mab (SEQ ID NO:32) and its derived amino acid sequence (SEQ ID NO:33).

nucleotide sequence of the constant human heavy chain of chD-A10 Mab (SEQ ID NO:48) and its derived amino acid sequence (SEQ ID NO:47).

nucleotide sequence of the constant human light chain of chD-A10 Mab (SEQ ID NO:50) and its derived amino acid sequence (SEQ ID NO:49).

The antibody CDR and FR regions have been determined according to various numbering approaches such as IMGT (ImMunoGeneTics Information System® http://imgt.cines.fr), Kabat or Common Numbering System. However, the IMGT determined CDRs for a given antibody are not necessarily identical to the CDRs defined by the other numbering systems. The variable domain CDRs and framework regions have been identified by the inventor—thanks to IMGT numbering systems.

Conversion of Chimeric Mab to Humanized Mab

The humanized H and L chain were generated using CDR-grafting by the PCR method. In order to generate a humanized antibody in which the CDRs of a mouse monoclonal antibody is grafted onto a human antibody, there is preferably to obtain a high homology between the variable region of a mouse monoclonal antibody and the variable region of a human antibody. Thus, the H chain and L chain V regions of a mouse anti-human CK8 monoclonal antibody are compared to the V region of all known human antibodies using the software IMGT/DomainGapAlign. When a mouse antibody is humanized by a conventional technology, the amino acid sequence of some of the V region FRs of a mouse antibody supporting the CDR may be grafted onto the FR of a human V region, as desired.

For both of the humanized H chain and L chain V regions, it is possible to select the L and H chain V regions (IGKV2-28*01, IGHV13-74*01) and J region, (IGKJ2*01, IGHJ4*01) respectively, having a high homology with the H and L chain V region and J region of the mD-A10. The variables regions of H and L of Hz D-A10 were amplified by PCR and cloned into the expression vector p3U containing the human IgG1 constant region.

In the case of murine CDR-grafted antibodies, the binding activity is decreased by grafting of the amino acid sequence of CDR in the human antibody alone. In order to avoid this reduction, among the amino acid residues in FR different between a human antibody and a mouse antibody, amino acid residues considered to have influences on the binding activity are grafted together with the amino acid sequence of CDR. Accordingly, an attempt was also made in this example to identify the amino acid residues in FR considered to have influences on the binding activity.

Following SDR grafting, the CDR sequences for VH and VL of Hz D-A10 Mab are shown in table 3.

Mab Reactivity to CK8 Peptides Determined by ELISA

The CK8 peptides, coupled or not with the bovine serum albumin (BSA) at the SH group of the C-terminal cysteine, were immobilized (0.5 µg/ml or 1 µg/ml respectively) at the bottom of the wells of a 96 well plate overnight at room temperature. Unbound peptides are washed away with purified water supplemented by Tween (Sigma, St Quentin Fallavier, France). The wells are then saturated with a saline phosphate buffer solution (PBS) containing 5% BSA for 2 hours at room temperature (RT). Then the plates are washed away with purified water supplemented by Tween. The Mab binding to the coated peptides is tested at different Mab concentrations following an incubation for 2 hours at RT in PBS (Invitrogen, Villebon sur Yvette, France) supplemented by 1% Bovine Serum Albumin (Sigma, St Quentin Fallavier, France). Unbound Mabs are washed away with purified water supplemented by Tween. The bound Mab are then revealed by an Goat anti-mouse IgG secondary antibody coupled to horse radish peroxidase (HRP), (Biorad, France). The absorbance is read at 450 nm and corrected at 630 nm. The specific requirements for the different experiments are detailed below.

MAb Reactivity to the Different Human CK8 Peptides 1 (SEQ ID No 1), 2 (SEQ ID No 2), 3 (SEQ ID No 3), 4 (SEQ ID No 4) and 17 (SEQ ID No 17)

The peptides 1, 2, 3 or 4 of human CK8 modified by addition of a C-terminal cysteine were coupled to BSA at the SH group of the C-terminal cysteine and immobilized at the bottom of a 96-wells plate. The complete human CK8 sequence comprising 483 amino acids (aa), (ref Uni-ProtKB P05787), is shown in FIG. 11. The positions of the sequences of peptides 1, 2, 3 and 4 are indicated by arrows gray and black on the human CK8 sequence:

```
Peptide 1 (SEQ ID No 1):
AEQRGELAIKDANAKLSELEAALQRAKQD-C
(aa 338 - aa 366)

Peptide 2 (SEQ ID No 2):
AEQRGELAIKDANAKLSELE-C
(aa 338 - aa 357)

Peptide 3 (SEQ ID No 3):
AALQRAKQD-C
(aa 358 - aa 366)
```

Peptide 4 (SEQ ID No 4): SELEAALQRAKQD-C (aa 354-aa 366)

Peptide 17 (SEQ ID No 17): C-AIKDANAKLSELEAALQRAKQD (aa 345-aa 366)

Different Mab concentrations (from 10 µg/mL then diluted at 1/10) were incubated for 2 hours at room temperature with either the peptide 1, peptide 2, peptide 3, peptide 4 or peptide 17. The optical density values (OD) was read at 450 nm and corrected at 630 nm. The results are shown in FIG. 12 and summarized in Table 7 below. These results clearly demonstrated a different mD-A10 reactivity profile compared to the M20 antibody.

TABLE 7

Mab reactivity with coated BSA conjugated peptide 1 to peptide 4 and peptide 17.

| Peptide (N°) | Sequence CK8 (aa) | MAb reactivity with coated BSA conjugated peptides | |
|---|---|---|---|
| | | M20 | D-A10 |
| Peptide 1 | 338-AEQRGELAIKDANAKLSELEAALQRAKQD-C-366 | + | +++ |
| Peptide 2 | 338-AEQRGELAIKDANAKLSELE-C-357 | − | − |
| Peptide 3 | 358-AALQRAKQD-C-366 | − | − |
| Peptide 4 | 354-SELEAALQRAKQD-C-366 | − | ++ |
| Peptide 17 | 345-C-AIKDANAKLSELEAALQRAKQD-366 | + | +++ |

The level of Mab reactivity to recognize or not the coated BSA conjugated peptides 1, 2, 3, 4 or 17 is respectively indicated by signs such as +++(strong), ++(medium), +(weak) or −(no).

MAb Reactivity for Different Coated Unconjugated Human CK8 Related Peptides 1, 5 to 28 (SEQ ID No 1, SEQ ID No 5 to SEQ ID No 28)

The unconjugated peptides 1, 5 to 28 of human CK8 were immobilized (2 µg/ml) at the bottom of a 96-wells plate. Different Mab concentrations (from 10 µg/mL then diluted at ¹/₁₀) were incubated for 2 hours at room temperature alone or with each peptide tested. The optical density values (OD) was read at 450 nm and corrected at 630 nm. The results are shown in FIG. 13A (related to mD-A10) or on FIG. 13B (related to M20). Comparative analysis is summarized in Table 8 below. These results clearly demonstrated a different mD-A10 reactivity profile compared to the M20 antibody against the peptide panel tested.

TABLE 8

Mab reactivity with different coated unconjugated peptides

| Peptide (No) | Sequence CK8 (aa) | Ab reactivity on coated free peptides | |
|---|---|---|---|
| | | D-A10 | M20 |
| Peptide 1 | 338-AEQRGELAIKDANAKLSELEAALQRAKQD-C-366 | +++ | + |
| Peptide 5 | 338-AEQRGELAIKDANAKLSELEAALQRAKQD-366 | +++ | + |

TABLE 8-continued

Mab reactivity with different coated unconjugated peptides

| Peptide (No) | Sequence CK8(aa) | Ab reactivity on coated free peptides | |
|---|---|---|---|
| | | D-A10 | M20 |
| Peptide 6 | 358-AALQRAKQD-366 | − | − |
| Peptide 7 | 357-EAALQRAKQD-366 | − | − |
| Peptide 8 | 356-LEAALQRAKQD-366 | − | − |
| Peptide 9 | 355-ELEAALQRAKQD-366 | − | − |
| Peptide 10 | 354-SELEAALQRAKQD-366 | − | − |
| Peptide 11 | 353-LSELEAALQRAKQD-366 | ++ | − |
| Peptide 12 | 352-KLSELEAALQRAKQD-366 | ++ | − |
| Peptide 13 | 351-AKLSELEAALQRAKQD-366 | ++ | − |
| Peptide 14 | 350-NAKLSELEAALQRAKQD-366 | +++ | − |
| Peptide 15 | 349-ANAKLSELEAALQRAKQD-366 | +++ | − |
| Peptide 16 | 348-DANAKLSELEAALQRAKQD-366 | +++ | − |
| Peptide 17 | 345-C-AIKDANAKLSELEAALQRAKQD-366 | +++ | − |
| Peptide 18 | 345-AIKDANAKLSELEAALQRAKQ-365 | +++ | − |
| Peptide 19 | 345-AIKDANAKLSELEAALQRAK-364 | +++ | − |
| Peptide 20 | 345-AIKDANAKLSELEAALQRA-363 | +++ | − |
| Peptide 21 | 345-AIKDANAKLSELEAALQR-362 | +++ | − |
| Peptide 22 | 345-AIKDANAKLSELEAALQ-361 | +++ | − |
| Peptide 23 | 345-AIKDANAKLSELEAAL-360 | +++ | − |
| Peptide 24 | 345-AIKDANAKLSELEAA-359 | − | − |
| Peptide 25 | 345-AIKDANAKLSELEA-358 | − | − |
| Peptide 26 | 345-AIKDANAKLSELE-357 | − | − |
| Peptide 27 | 345-AIKDANAKLSEL-356 | − | − |
| Peptide 28 | 345-AIKDANAKLSE-355 | − | − |

The level of Mab reactivity to recognize or not the coated unconjugated peptides is respectively indicated by signs such as +++ (strong), ++ (medium), + (weak) or − (no).

Effect of Free Peptides 1, 5 to 28 (SEQ ID No 1, SEQ ID No 5 to SEQ ID No 28) on the mD-A10 Mab to the Coated BSA Conjugate Peptide 1 or 17.

When setting competition assays of mD-A10 Mab with different CK8 peptides, the peptide-antibody mixture was incubated for 30 minutes before being placed in the presence of the peptide to detect that was immobilized at the bottom of the wells. The mD-A10 Mab was either placed in the presence of peptides 1, 5 to 28 (SEQ ID No 1, SEQ ID No 5 to SEQ ID No 28) for the recognition of BSA conjugated peptide 1 (SEQ ID No 1) or for the recognition of BSA conjugated peptide 17 (SEQ ID No 17).

Figure 14:
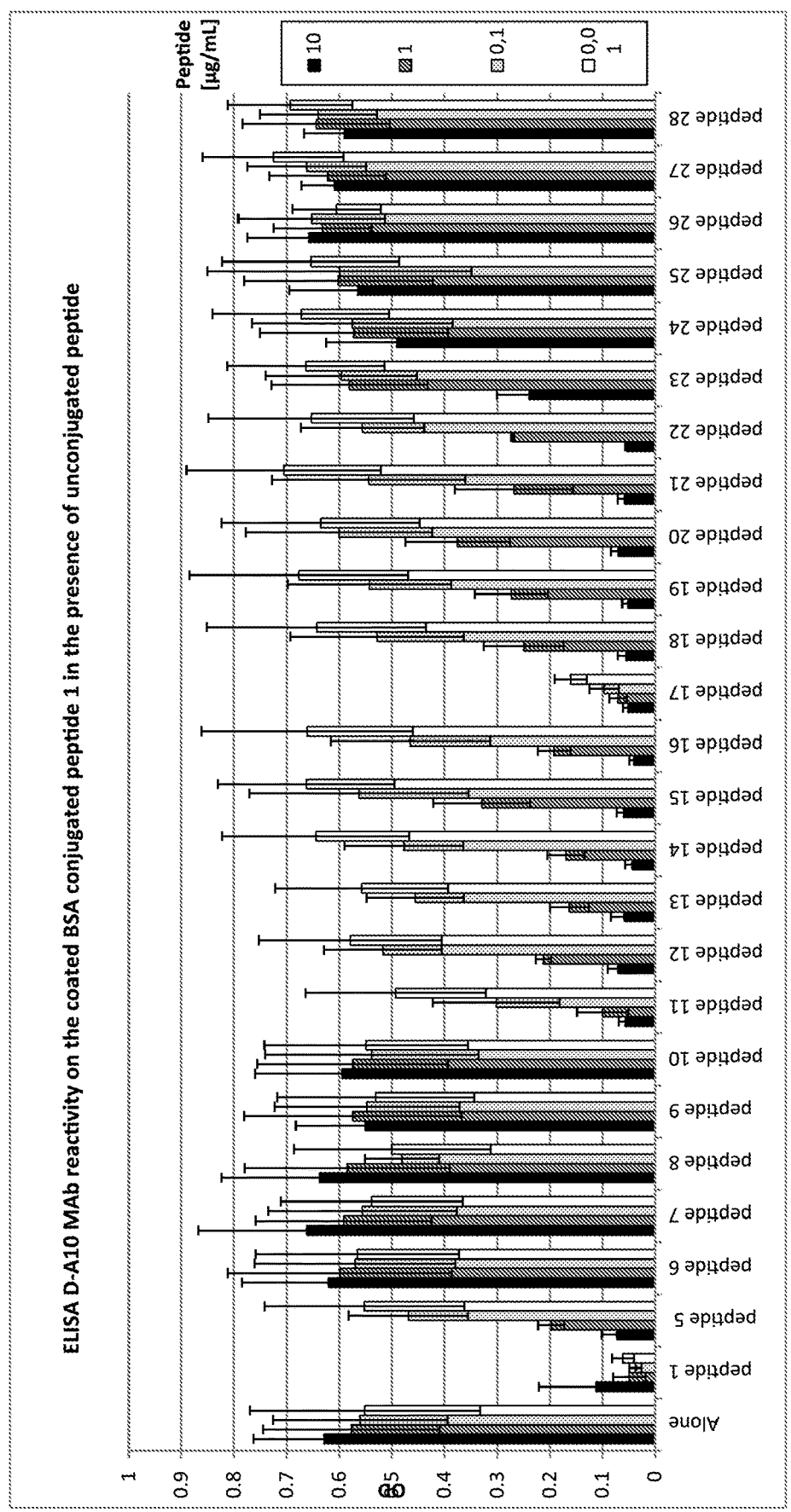
FIG. 14 illustrates the effect of unconjugated peptides 1 and 5 to 28 (SEQ ID NO: 1, SEQ ID NO: 5 to SEQ ID NO: 28) on the mD-A10 Mab recognition of the BSA conjugated peptide 1 (SEQ ID NO: 1) by ELISA.
Figure 15:
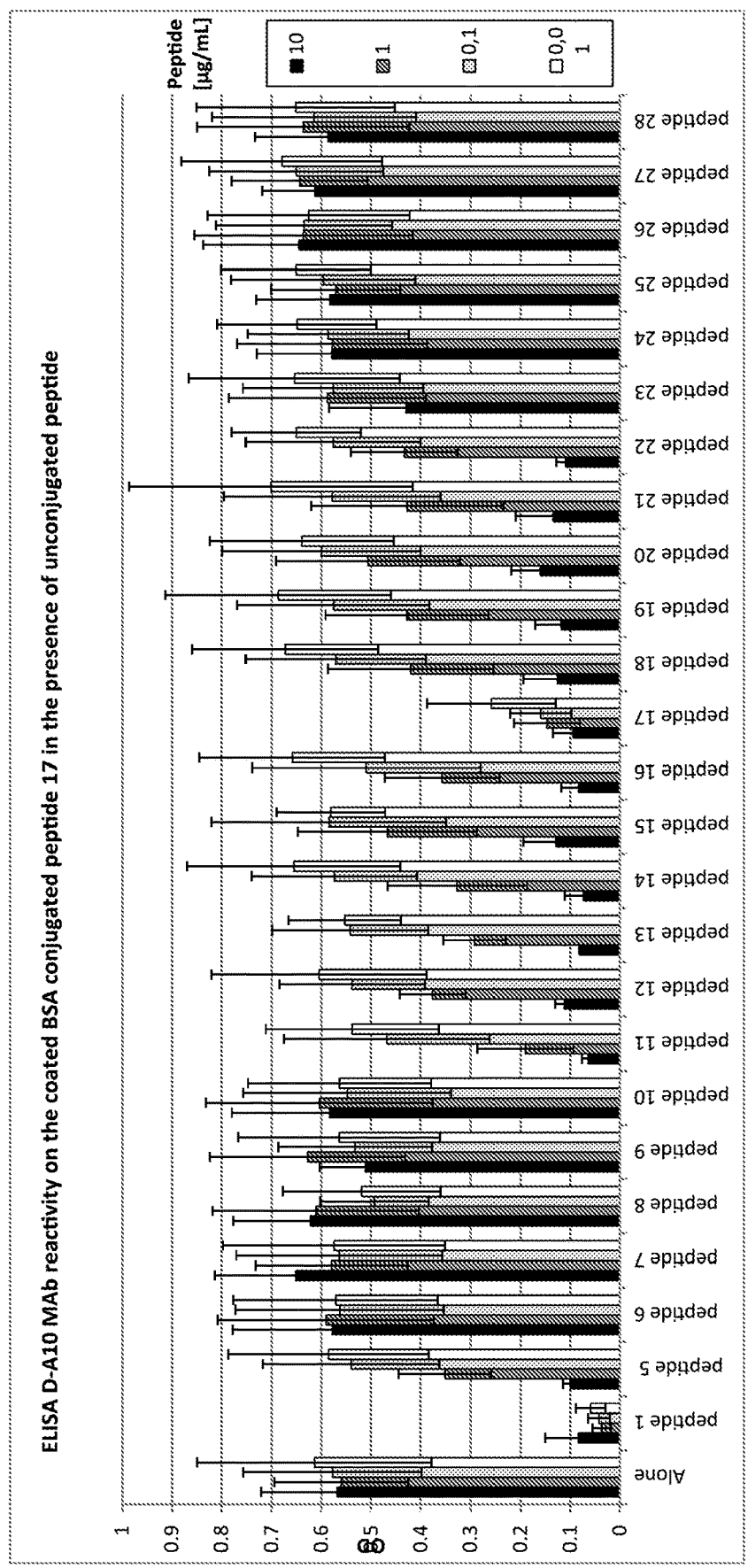
FIG. 15 illustrates the effect of unconjugated peptides 1, 5 to 28 (SEQ ID NO:1, SEQ ID NO: 5 to SEQ ID NO: 28) on the mD-A10 Mab on recognition of BSA conjugated peptide 17 (SEQ ID NO: 17) by ELISA.

The peptide 1 of human CK 8 modified by addition of a cysteine in position C-terminal was coupled to BSA at the SH group of its C-terminal cysteine and was immobilized at the bottom of the 96-wells plate. The murine monoclonal antibody D-A10 at a concentration of 1 ng/mL was incubated for 30 minutes in the presence of peptides 1, 5 to 28 at different concentrations (10, 1, 0.1 or 0.01 µg/mL). The peptide-antibody mixture or the antibody alone was then added and kept for 2 h at room temperature with the coated BSA conjugated peptide 1 or with the coated BSA conjugated peptide 17 and used for detection by ELISA. The optical density values (OD) was read at 450 nm and corrected at 630 nm. The results are shown in FIG. 14 with the coated BSA conjugated peptide 1 or in FIG. 15 with the coated BSA conjugated peptide 17.

The invention claimed is:

1. An antibody, or antibody fragment thereof, specifically binding the peptide having the amino acid sequence of SEQ ID NO: 29, said antibody comprising:
 a heavy chain comprising the following three CDRs, respectively CDR-H1, CDR-H2 and CDR-H3, wherein:
  CDR-H1 comprises the sequence SEQ ID NO: 37; and
  CDR-H2 comprises the sequence SEQ ID NO: 38; and
  CDR-H3 comprises the sequence SEQ ID NO: 39; and
 a light chain comprising the following three CDRs, respectively CDR-L1, CDR-L2 and CDR-L3, wherein:
  CDR-L1 comprises the sequence SEQ ID NO: 34; and
  CDR-L2 comprises the sequence SEQ ID NO: 35; and
  CDR-L3 comprises the sequence SEQ ID NO: 36;
 wherein the light chain comprises the sequence SEQ ID NO: 31, or a sequence with at least 80% identity after optimal alignment with sequence SEQ ID NO: 31, and the heavy chain comprises the sequence SEQ ID NO: 33, or a sequence with at least 80% identity after optimal alignment with sequence SEQ ID NO: 33.

2. The antibody or antibody fragment according to claim 1, wherein said antibody is a monoclonal antibody.

3. The antibody or antibody fragment according to claim 1, wherein said antibody or antibody fragment is humanized.

4. A humanized antibody, or antibody fragment thereof, specifically binding the peptide having the amino acid sequence of SEQ ID NO: 29, said antibody comprising:
 a heavy chain comprising the following three CDRs, respectively CDR-H1', CDR-H2' and CDR-H3', wherein:
  CDR-H1' comprises the sequence SEQ ID NO: 40; and
  CDR-H2' comprises the sequence SEQ ID NO: 41; and
  CDR-H3' comprises the sequence SEQ ID NO: 39; and
 a light chain comprising the following three CDRs, respectively CDR-L1', CDR-L2' and CDR-L3', wherein:
  CDR-L1' comprises the sequence SEQ ID NO: 42; and
  CDR-L2' comprises the sequence SEQ ID NO: 35; and
  CDR-L3' comprises the sequence SEQ ID NO: 36;
 wherein the heavy chain comprises the sequence SEQ ID NO: 44, or a sequence with at least 80% identity after optimal alignment with sequence SEQ ID NO: 44, and the light chain comprises the sequence SEQ ID NO: 43, or a sequence with at least 80% identity after optimal alignment with sequence SEQ ID NO: 43.

5. A pharmaceutical composition or a diagnostic kit, comprising an antibody or antibody fragment according to claim 1, wherein the pharmaceutical composition comprises a suitable pharmaceutical carrier.

6. The pharmaceutical composition or kit according to claim 5, wherein the antibody or antibody fragment is selected from the group consisting of Fv, Fab, F(ab')2, scFv, and a monoclonal antibody.

7. A method for treating colorectal cancer, comprising administering an effective amount of an antibody or antibody fragment according to claim 1 to a subject having a cancer whose cells express CK8 protein, to thereby treat the cancer.

8. A method for treating colorectal cancer, comprising administering an effective amount of an antibody or antibody fragment according to claim 4 to a subject having a cancer whose cells express CK8 protein, to thereby treat the cancer.

9. A method for inducing caspase 3 dependent cell apoptosis of colorectal cancer cells expressing CK8 protein, comprising administering an effective amount of an antibody or antibody fragment according to claim 1 to a subject having a colorectal cancer that expresses CK8 protein.

10. A method for inducing caspase 3 dependent cell apoptosis of colorectal cancer cells expressing CK8 protein, comprising administering an effective amount of an antibody or antibody fragment according to claim 4 to a subject having a colorectal cancer that expresses CK8 protein.

11. The humanized antibody or antibody fragment thereof according to claim 4, wherein the heavy chain further comprises a constant region comprising the sequence SEQ ID NO: 47, and wherein the light chain further comprises a constant region comprising the sequence SEQ ID NO: 49.

12. The antibody or antibody fragment of claim 1, wherein the light chain comprises a sequence with at least 90% identity after optimal alignment with sequence SEQ ID NO: 31, and the heavy chain comprises a sequence with at least 90% identity after optimal alignment with sequence SEQ ID NO: 33.

13. The antibody or antibody fragment of claim 1, wherein the light chain comprises a sequence with 100% identity after optimal alignment with the sequence SEQ ID NO: 31, and the heavy chain comprises a sequence with 100% identity after optimal alignment with the sequence SEQ ID NO: 33.

14. The humanized antibody or antibody fragment of claim 4, wherein the heavy chain comprises a sequence with at least 90% identity after optimal alignment with sequence SEQ ID NO: 44, and the light chain comprises a sequence with at least 90% identity after optimal alignment with sequence SEQ ID NO: 43.

15. The humanized antibody or antibody fragment of claim 4, wherein the heavy chain comprises a sequence with 100% identity after optimal alignment with the sequence SEQ ID NO: 44, and the light chain comprises a sequence with 100% identity after optimal alignment with the sequence SEQ ID NO: 43.

16. The humanized antibody or antibody fragment thereof according to claim 15, wherein the heavy chain further comprises a constant region comprising the sequence SEQ ID NO: 47, and wherein the light chain further comprises a constant region comprising the sequence SEQ ID NO: 49.

17. A pharmaceutical composition or a diagnostic kit, comprising a humanized antibody or antibody fragment according to claim 4, wherein the pharmaceutical composition comprises a suitable pharmaceutical carrier.

18. The pharmaceutical composition or the diagnostic kit according to claim 17, wherein the humanized antibody or antibody fragment is selected from the group consisting of Fv, Fab, F(ab')2, scFv, and a monoclonal antibody.

* * * * *

UNITED STATES PATENT AND TRADEMARK OFFICE
CERTIFICATE OF CORRECTION

PATENT NO. : 10,533,046 B2
APPLICATION NO. : 15/502469
DATED : January 14, 2020
INVENTOR(S) : Marie Alexandra Albaret et al.

Page 1 of 1

It is certified that error appears in the above-identified patent and that said Letters Patent is hereby corrected as shown below:

On the Title Page

At item (73) delete the text "INTERNATIONA" and substitute therefore, --INTERNATIONAL--.

Signed and Sealed this
Fifth Day of May, 2020

Andrei Iancu
*Director of the United States Patent and Trademark Office*